United States Patent
Hwang et al.

(10) Patent No.: US 10,793,900 B2
(45) Date of Patent: Oct. 6, 2020

(54) POLYPEPTIDE SPECIFICALLY BINDING TO TAQ DNA POLYMERASE AND USE THEREOF

(71) Applicants: ENZYNOMICS CO. LTD., Daejeon (KR); KOREA ADVANCED INSTITUTE OF SCIENCE AND TECHNOLOGY, Daejeon (KR)

(72) Inventors: Da-Eun Hwang, Daejeon (KR); Yong Keol Shin, Daejeon (KR); Palinda Ruvan Munashingha, Daejeon (KR); So Yeon Park, Daejeon (KR); Yeon-Soo Seo, Daejeon (KR); Hak-Sung Kim, Daejeon (KR)

(73) Assignees: ENZYNOMICS CO. LTD., Daejeon (KR); KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 234 days.

(21) Appl. No.: 15/575,886

(22) PCT Filed: Apr. 21, 2017

(86) PCT No.: PCT/KR2017/004289
§ 371 (c)(1),
(2) Date: Nov. 21, 2017

(87) PCT Pub. No.: WO2017/188668
PCT Pub. Date: Nov. 2, 2017

(65) Prior Publication Data
US 2018/0298422 A1 Oct. 18, 2018

(30) Foreign Application Priority Data
Apr. 25, 2016 (KR) ............ 10-2016-0049832

(51) Int. Cl.
*C07K 14/195* (2006.01)
*C12Q 1/686* (2018.01)
*C07K 14/725* (2006.01)

(52) U.S. Cl.
CPC ............ *C12Q 1/686* (2013.01); *C07K 14/195* (2013.01); *C07K 14/7051* (2013.01); *C07K 2319/00* (2013.01)

(58) Field of Classification Search
None
See application file for complete search history.

(56) References Cited

U.S. PATENT DOCUMENTS 10,017,570 B2 * 7/2018 Kim .................. C07K 14/705
2015/0094450 A1 * 4/2015 Kim .................. C07K 14/195
530/350

FOREIGN PATENT DOCUMENTS

KR 10-1488110 B1 1/2015

OTHER PUBLICATIONS

Lee JH, Choi HH, Yun M, Kang Y, Jung JE, Ryu Y, Kim TY, Cha YJ, Cho HS, Min JJ, Chung CW, Kim HS. Enzymatic prenylation and oxime ligation for the synthesis of stable and homogeneous protein-drug conjugates for targeted therapy. Angew Chem Int Ed Engl. Oct. 5, 2015; 54(41):12020-4. (Year: 2015).*
GenPept Accession No. 4UIP_B Chain B, Repebody (RAC1) (submitted Mar. 2015, retrieved on Sep. 4, 2019 from https://www.ncbi.nlm.nih.gov/protein/4UIP_B). (Year: 2015).*
Ngo et al. In the Protein Folding Problem and Tertiary Structure Prediction, 1994, Merz et al. (ed.), Birkhauser, Boston, MA, pp. 433 and 492-495.*
Wang et al., ChemComm, vol. 52, pp. 1064-10687, 2016.*
D'Aquila et al., "Maximizing sensitivity and specificity of PCR by pre-amplification heating", Nucleic Acids Research, vol. 19, No. 13, p. 3749, (1991).
Scalice et al., "Monoclonal antibodies prepared against the DNA polymerase from Thermus aquaticus are potent inhibitors of enzyme activity", Journal of Immunological Methods, vol. 172, pp. 147-163, (1994).

* cited by examiner

*Primary Examiner* — Richard G Hutson
(74) *Attorney, Agent, or Firm* — Vorys, Sater, Seymour & Pease LLP; Mih Suhn Koh

(57) ABSTRACT

The present invention discloses a novel polypeptide capable of binding Taq DNA polymerase, a polynucleotide encoding the polypeptide, a recombinant vector comprising the polynucleotide, a cell having the recombinant vector introduced therein, a method of producing the polypeptide using the recombinant cell, and a hot-start PCR composition comprising the polypeptide. The polypeptide of the present invention is capable of binding specifically to Taq DNA polymerase to inhibit the activity of the polymerase, and thus may be effectively used in hot-start PCR using Taq DNA polymerase.

10 Claims, 6 Drawing Sheets

Specification includes a Sequence Listing.

[FIG. 1]
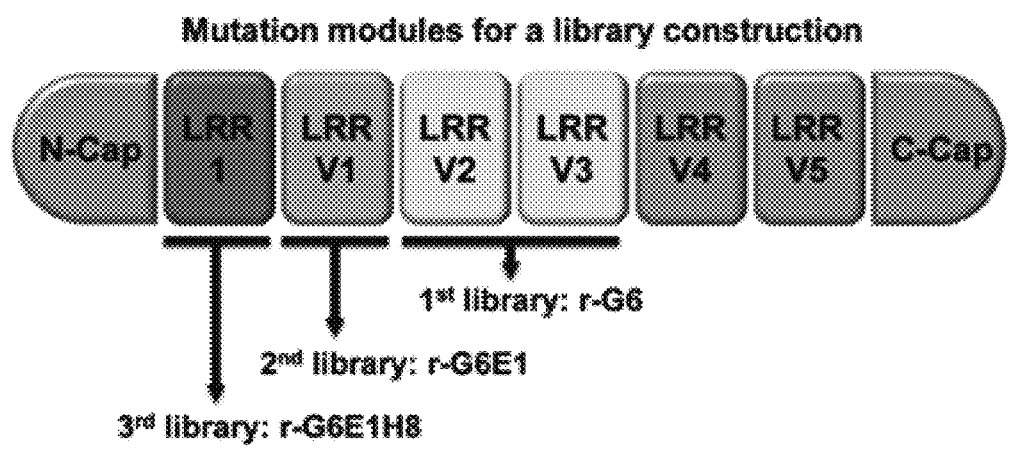
[FIG. 2]
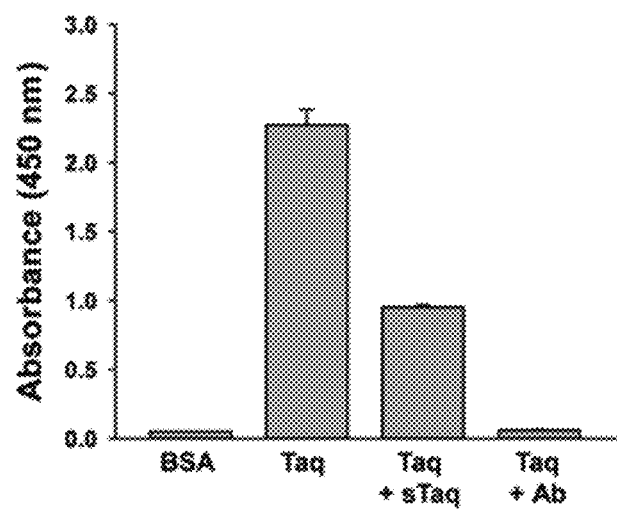

[FIG. 3]

| Repebody | Substituted residues | | | | | | | | | | | | | K_D (nM) |
|---|---|---|---|---|---|---|---|---|---|---|---|---|---|
| | LRR1 module | | | | LRRV1 module | | | | LRRV2 module | | | LRRV3 module | |
| | 45 | 47 | 49 | 50 | 67 | 69 | 71 | 72 | 91 | 93 | 94 | 115 | 117 | 118 | |
| Template | Q | I | N | N | Y | A | G | G | I | T | G | V | V | E | - |
| First round selection (LRRV2, LRRV3 modules) | | | | | | | | | | | | | | | |
| r-G6 | | | | | | | | | S | W | L | S | H | W | 134.4 ± 21.1 |
| Second round selection (LRRV1 module) | | | | | | | | | | | | | | | |
| r-G6E1 | | | | | | R | K | G | A | | | | | | 37.5 ± 6.0 |
| r-G6E3 | | | | | | K | K | G | A | | | | | | 45.5 ± 17.5 |
| r-G6D9 | | | | | | A | K | G | A | | | | | | 66.7 ± 15.6 |
| Third round selection (LRR1 module) | | | | | | | | | | | | | | | |
| r-G6E1 A1 | Y | A | I | N | | | | | | | | | | | 12.6 ± 5.7 |
| r-G6E1 A8 | R | T | M | N | | | | | | | | | | | 12.9 ± 5.0 |
| r-G6E1 B11 | N | Q | N | N | | | | | | | | | | | 34.3 ± 9.0 |
| r-G6E1 F11 | V | T | I | N | | | | | | | | | | | 15.3 ± 9.7 |
| r-G6E1 H6 | R | K | L | N | | | | | | | | | | | 10.9 ± 5.4 |
| r-G6E1 H7 | S | T | H | N | | | | | | | | | | | 67.6 ± 40.1 |
| r-G6E1 H8 | S | K | I | N | | | | | | | | | | | 10.3 ± 8.2 |

[FIG. 4]
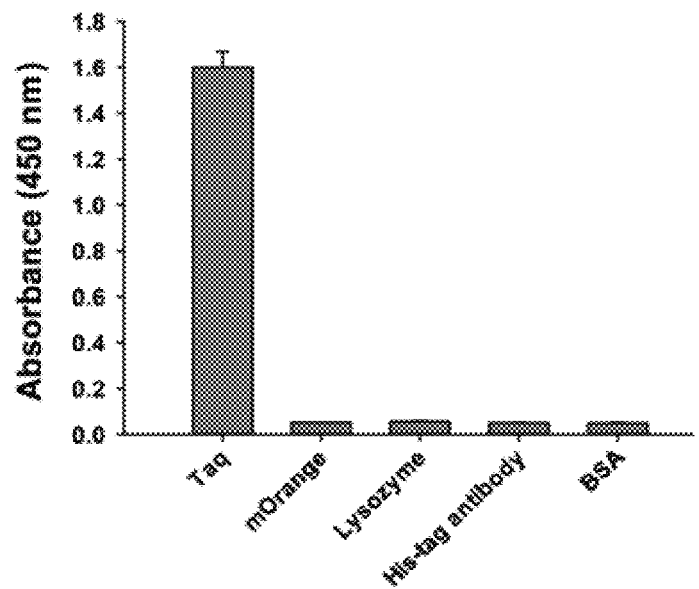
[FIG. 5]
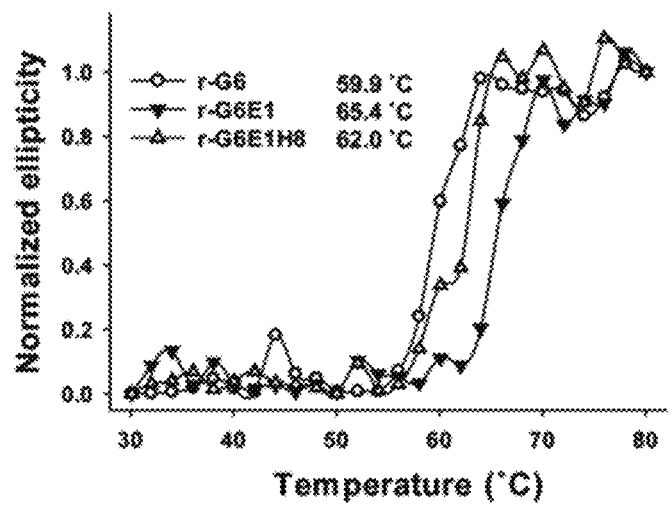

[FIG. 6]
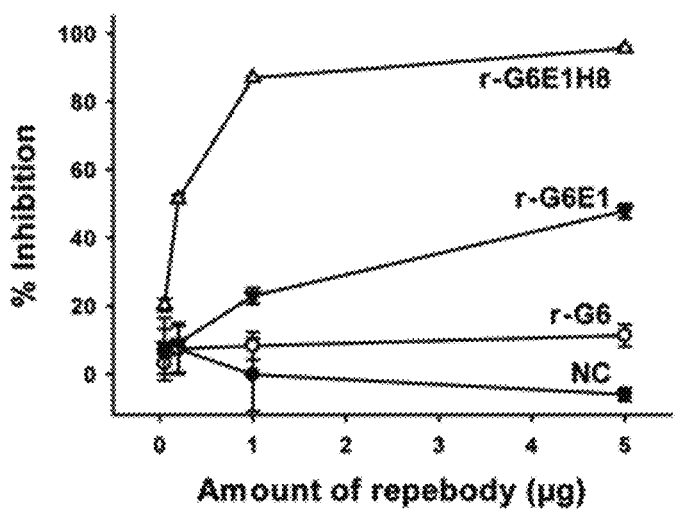
[FIG. 7]
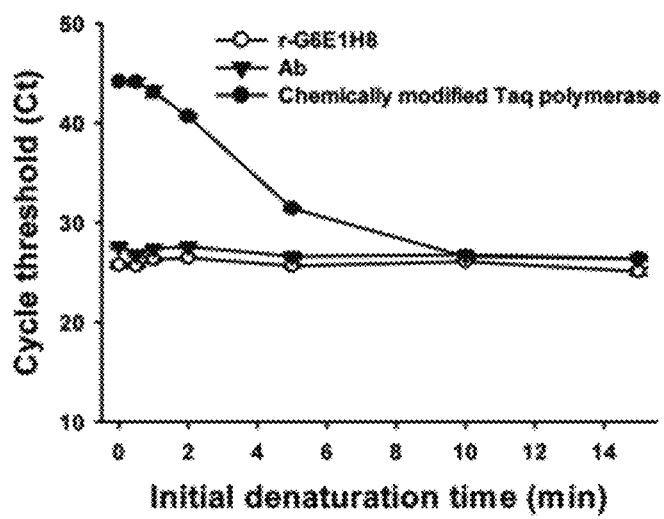

[FIG. 8]
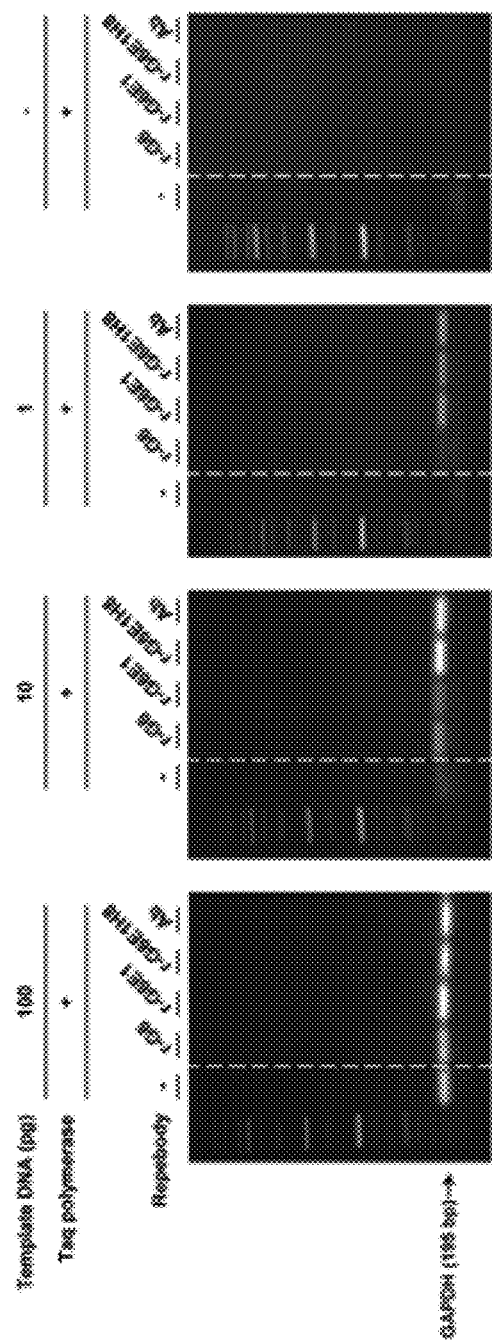

[FIG. 9]
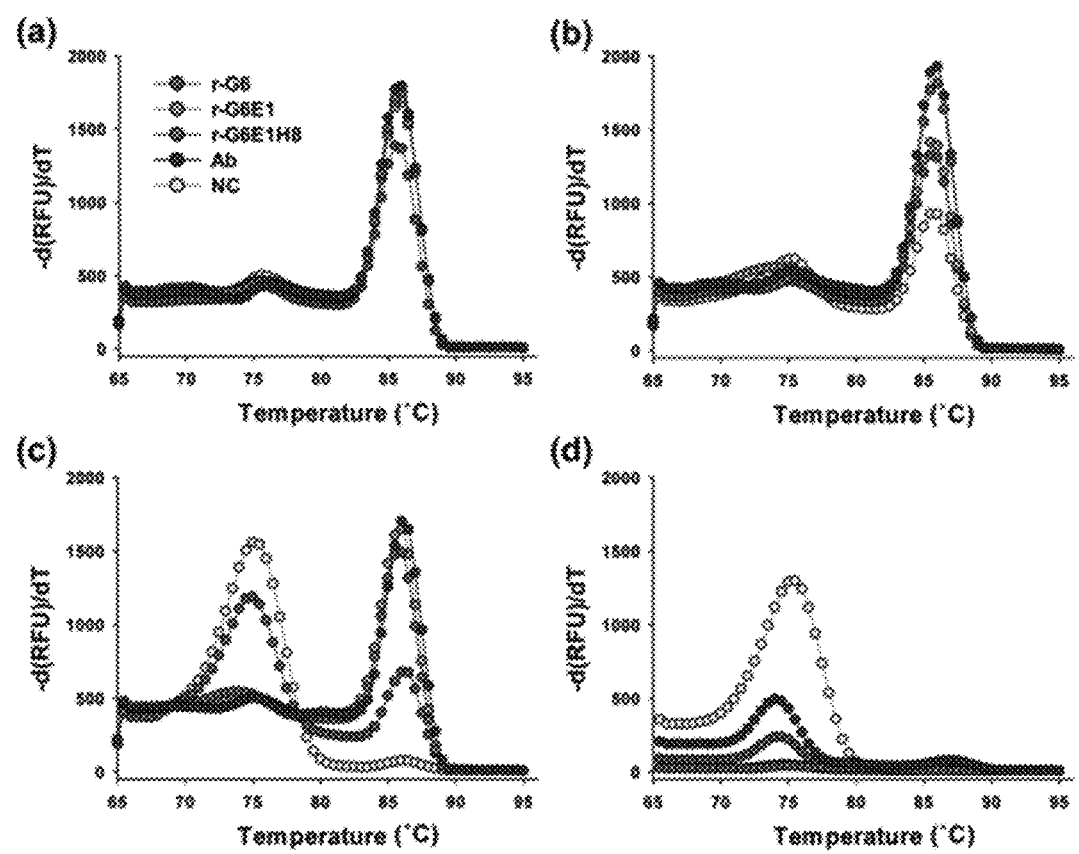
[FIG. 10]
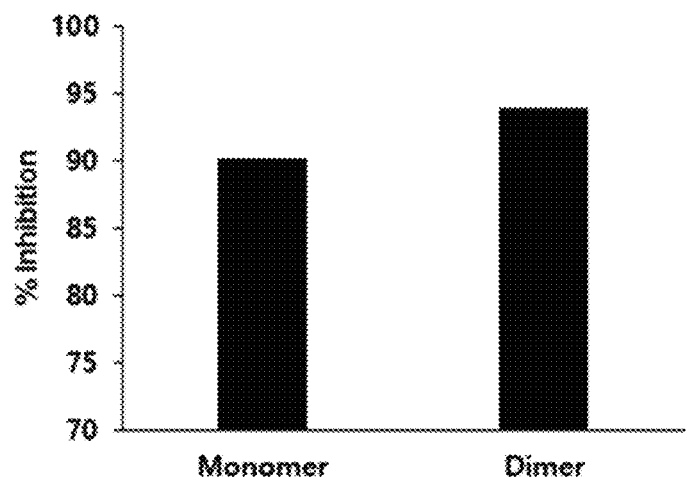

SEQUENCE LISTING

```
<160> NUMBER OF SEQ ID NOS: 25

<210> SEQ ID NO 1
<211> LENGTH: 242
<212> TYPE: PRT
<213> ORGANISM: Artificial Sequence
<220> FEATURE:
<223> OTHER INFORMATION: Taq Polymerase Repebody
<220> FEATURE:
<221> NAME/KEY: BINDING
<222> LOCATION: (45)
<223> OTHER INFORMATION: X= Q, S, R, Y, V or N
<220> FEATURE:
<221> NAME/KEY: BINDING
<222> LOCATION: (47)
<223> OTHER INFORMATION: X= I, T, K, A or Q
<220> FEATURE:
<221> NAME/KEY: BINDING
<222> LOCATION: (49)
<223> OTHER INFORMATION: X= N, H, L, M or I
<220> FEATURE:
<221> NAME/KEY: BINDING
<222> LOCATION: (67)
<223> OTHER INFORMATION: X= Y, R, A or K
<220> FEATURE:
<221> NAME/KEY: BINDING
<222> LOCATION: (69)
<223> OTHER INFORMATION: X= A or K
<220> FEATURE:
<221> NAME/KEY: BINDING
<222> LOCATION: (72)
<223> OTHER INFORMATION: X= G or A
<220> FEATURE:
<221> NAME/KEY: BINDING
<222> LOCATION: (91)
<223> OTHER INFORMATION: X= I or S
<220> FEATURE:
<221> NAME/KEY: BINDING
<222> LOCATION: (93)
<223> OTHER INFORMATION: X= T or W
<220> FEATURE:
<221> NAME/KEY: BINDING
<222> LOCATION: (94)
<223> OTHER INFORMATION: X= G or L
<220> FEATURE:
<221> NAME/KEY: BINDING
<222> LOCATION: (115)
<223> OTHER INFORMATION: X= V or S
<220> FEATURE:
<221> NAME/KEY: BINDING
<222> LOCATION: (117)
<223> OTHER INFORMATION: X= V or H
<220> FEATURE:
<221> NAME/KEY: BINDING
<222> LOCATION: (118)
<223> OTHER INFORMATION: X= E or W

<400> SEQUENCE: 1

Glu Thr Ile Thr Val Ser Thr Pro Ile Lys Gln Ile Phe Pro Asp Asp
1               5                   10                  15
```

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Xaa Ile Xaa Ala
        35                  40                  45

Xaa Asn Ser Asp Ile Lys Ser Val Gln Gly Ile Gln Tyr Leu Pro Asn
50                  55                  60

Val Arg Xaa Leu Xaa Leu Gly Xaa Asn Lys Leu His Asp Ile Ser Ala
65                  70                  75                  80

Leu Lys Glu Leu Thr Asn Leu Thr Tyr Leu Xaa Leu Xaa Xaa Asn Gln
                85                  90                  95

Leu Gln Ser Leu Pro Asn Gly Val Phe Asp Lys Leu Thr Asn Leu Lys
            100                 105                 110

Glu Leu Xaa Leu Xaa Xaa Asn Gln Leu Gln Ser Leu Pro Asp Gly Val
            115                 120                 125

Phe Asp Lys Leu Thr Asn Leu Thr Glu Leu Asp Leu Ser Tyr Asn Gln
130                 135                 140

Leu Gln Ser Leu Pro Glu Gly Val Phe Asp Lys Leu Thr Gln Leu Lys
145                 150                 155                 160

Asp Leu Arg Leu Tyr Gln Asn Gln Leu Lys Ser Val Pro Asp Gly Val
                165                 170                 175

Phe Asp Arg Leu Thr Ser Leu Gln Tyr Ile Trp Leu His Asp Asn Pro
            180                 185                 190

Trp Asp Cys Thr Cys Pro Gly Ile Arg Tyr Leu Ser Glu Trp Ile Asn
            195                 200                 205

Lys His Ser Gly Val Val Arg Asn Ser Ala Gly Ser Val Ala Pro Asp
        210                 215                 220

Ser Ala Lys Cys Ser Gly Ser Gly Lys Pro Val Arg Ser Ile Ile Cys
225                 230                 235                 240

Pro Thr

<210> SEQ ID NO 2
<211> LENGTH: 242
<212> TYPE: PRT
<213> ORGANISM: Artificial Sequence
<220> FEATURE:
<223> OTHER INFORMATION: Taq Polymerase Repebody 3RFS

<400> SEQUENCE: 2

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ala
        35                  40                  45

Asn Asn Ser Asp Ile Lys Ser Val Gln Gly Ile Gln Tyr Leu Pro Asn
50                  55                  60

Val Arg Tyr Leu Ala Leu Gly Gly Asn Lys Leu His Asp Ile Ser Ala
65                  70                  75                  80

Leu Lys Glu Leu Thr Asn Leu Thr Tyr Leu Ile Leu Thr Gly Asn Gln
                85                  90                  95

Leu Gln Ser Leu Pro Asn Gly Val Phe Asp Lys Leu Thr Asn Leu Lys
            100                 105                 110

Glu Leu Val Leu Val Glu Asn Gln Leu Gln Ser Leu Pro Asp Gly Val
            115                 120                 125

-continued

```
Phe Asp Lys Leu Thr Asn Leu Thr Glu Leu Asp Leu Ser Tyr Asn Gln
    130                 135                 140

Leu Gln Ser Leu Pro Glu Gly Val Phe Asp Lys Leu Thr Gln Leu Lys
145                 150                 155                 160

Asp Leu Arg Leu Tyr Gln Asn Gln Leu Lys Ser Val Pro Asp Gly Val
                165                 170                 175

Phe Asp Arg Leu Thr Ser Leu Gln Tyr Ile Trp Leu His Asp Asn Pro
            180                 185                 190

Trp Asp Cys Thr Cys Pro Gly Ile Arg Tyr Leu Ser Glu Trp Ile Asn
        195                 200                 205

Lys His Ser Gly Val Val Arg Asn Ser Ala Gly Ser Val Ala Pro Asp
    210                 215                 220

Ser Ala Lys Cys Ser Gly Ser Gly Lys Pro Val Arg Ser Ile Ile Cys
225                 230                 235                 240

Pro Thr
```

<210> SEQ ID NO 3
<211> LENGTH: 242
<212> TYPE: PRT
<213> ORGANISM: Artificial Sequence
<220> FEATURE:
<223> OTHER INFORMATION: Taq Polymerase Repebody r-G6

<400> SEQUENCE: 3

```
Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45

Asn Asn Ser Asp Ile Lys Ser Val Gln Gly Ile Gln Tyr Leu Pro Asn
    50                  55                  60

Val Arg Tyr Leu Ala Leu Gly Gly Asn Lys Leu His Asp Ile Ser Ala
65                  70                  75                  80

Leu Lys Glu Leu Thr Asn Leu Thr Tyr Leu Ser Leu Trp Leu Asn Gln
                85                  90                  95

Leu Gln Ser Leu Pro Asn Gly Val Phe Asp Lys Leu Thr Asn Leu Lys
            100                 105                 110

Glu Leu Ser Leu His Trp Asn Gln Leu Gln Ser Leu Pro Asp Gly Val
        115                 120                 125

Phe Asp Lys Leu Thr Asn Leu Thr Glu Leu Asp Leu Ser Tyr Asn Gln
    130                 135                 140

Leu Gln Ser Leu Pro Glu Gly Val Phe Asp Lys Leu Thr Gln Leu Lys
145                 150                 155                 160

Asp Leu Arg Leu Tyr Gln Asn Gln Leu Lys Ser Val Pro Asp Gly Val
                165                 170                 175

Phe Asp Arg Leu Thr Ser Leu Gln Tyr Ile Trp Leu His Asp Asn Pro
            180                 185                 190

Trp Asp Cys Thr Cys Pro Gly Ile Arg Tyr Leu Ser Glu Trp Ile Asn
        195                 200                 205

Lys His Ser Gly Val Val Arg Asn Ser Ala Gly Ser Val Ala Pro Asp
    210                 215                 220

Ser Ala Lys Cys Ser Gly Ser Gly Lys Pro Val Arg Ser Ile Ile Cys
225                 230                 235                 240

Pro Thr
```

<210> SEQ ID NO 4
<211> LENGTH: 242
<212> TYPE: PRT
<213> ORGANISM: Artificial Sequence
<220> FEATURE:
<223> OTHER INFORMATION: Taq Polymerase Repebody r-G6E1

<400> SEQUENCE: 4

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45

Asn Asn Ser Asp Ile Lys Ser Val Gln Gly Ile Gln Tyr Leu Pro Asn
    50                  55                  60

Val Arg Arg Leu Lys Leu Gly Ala Asn Lys Leu His Asp Ile Ser Ala
65                  70                  75                  80

Leu Lys Glu Leu Thr Asn Leu Thr Tyr Leu Ser Leu Trp Leu Asn Gln
                85                  90                  95

Leu Gln Ser Leu Pro Asn Gly Val Phe Asp Lys Leu Thr Asn Leu Lys
            100                 105                 110

Glu Leu Ser Leu His Trp Asn Gln Leu Gln Ser Leu Pro Asp Gly Val
        115                 120                 125

Phe Asp Lys Leu Thr Asn Leu Thr Glu Leu Asp Leu Ser Tyr Asn Gln
    130                 135                 140

Leu Gln Ser Leu Pro Glu Gly Val Phe Asp Lys Leu Thr Gln Leu Lys
145                 150                 155                 160

Asp Leu Arg Leu Tyr Gln Asn Gln Leu Lys Ser Val Pro Asp Gly Val
                165                 170                 175

Phe Asp Arg Leu Thr Ser Leu Gln Tyr Ile Trp Leu His Asp Asn Pro
            180                 185                 190

Trp Asp Cys Thr Cys Pro Gly Ile Arg Tyr Leu Ser Glu Trp Ile Asn
        195                 200                 205

Lys His Ser Gly Val Val Arg Asn Ser Ala Gly Ser Val Ala Pro Asp
    210                 215                 220

Ser Ala Lys Cys Ser Gly Ser Gly Lys Pro Val Arg Ser Ile Ile Cys
225                 230                 235                 240

Pro Thr

<210> SEQ ID NO 5
<211> LENGTH: 242
<212> TYPE: PRT
<213> ORGANISM: Artificial Sequence
<220> FEATURE:
<223> OTHER INFORMATION: Taq Polymerase Repebody r-G6E3

<400> SEQUENCE: 5

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45

Asn Asn Ser Asp Ile Lys Ser Val Gln Gly Ile Gln Tyr Leu Pro Asn
    50                  55                  60

```
Val Arg Lys Leu Lys Leu Gly Ala Asn Lys Leu His Asp Ile Ser Ala
65                  70                  75                  80

Leu Lys Glu Leu Thr Asn Leu Thr Tyr Leu Ser Leu Trp Leu Asn Gln
                85                  90                  95

Leu Gln Ser Leu Pro Asn Gly Val Phe Asp Lys Leu Thr Asn Leu Lys
            100                 105                 110

Glu Leu Ser Leu His Trp Asn Gln Leu Gln Ser Leu Pro Asp Gly Val
        115                 120                 125

Phe Asp Lys Leu Thr Asn Leu Thr Glu Leu Asp Leu Ser Tyr Asn Gln
    130                 135                 140

Leu Gln Ser Leu Pro Glu Gly Val Phe Asp Lys Leu Thr Gln Leu Lys
145                 150                 155                 160

Asp Leu Arg Leu Tyr Gln Asn Gln Leu Lys Ser Val Pro Asp Gly Val
                165                 170                 175

Phe Asp Arg Leu Thr Ser Leu Gln Tyr Ile Trp Leu His Asp Asn Pro
            180                 185                 190

Trp Asp Cys Thr Cys Pro Gly Ile Arg Tyr Leu Ser Glu Trp Ile Asn
        195                 200                 205

Lys His Ser Gly Val Val Arg Asn Ser Ala Gly Ser Val Ala Pro Asp
    210                 215                 220

Ser Ala Lys Cys Ser Gly Ser Gly Lys Pro Val Arg Ser Ile Ile Cys
225                 230                 235                 240

Pro Thr

<210> SEQ ID NO 6
<211> LENGTH: 242
<212> TYPE: PRT
<213> ORGANISM: Artificial Sequence
<220> FEATURE:
<223> OTHER INFORMATION: Taq Polymerase Repebody r-G6D9

<400> SEQUENCE: 6

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
                20                  25                  30

Asp Ala Val Thr Gln Asn Glu Leu Asn Ser Ile Asp Gln Ile Ile Ala
            35                  40                  45

Asn Asn Ser Asp Ile Lys Ser Val Gln Gly Ile Gln Tyr Leu Pro Asn
        50                  55                  60

Val Arg Ala Leu Lys Leu Gly Ala Asn Lys Leu His Asp Ile Ser Ala
65                  70                  75                  80

Leu Lys Glu Leu Thr Asn Leu Thr Tyr Leu Ser Leu Trp Leu Asn Gln
                85                  90                  95

Leu Gln Ser Leu Pro Asn Gly Val Phe Asp Lys Leu Thr Asn Leu Lys
            100                 105                 110

Glu Leu Ser Leu His Trp Asn Gln Leu Gln Ser Leu Pro Asp Gly Val
        115                 120                 125

Phe Asp Lys Leu Thr Asn Leu Thr Glu Leu Asp Leu Ser Tyr Asn Gln
    130                 135                 140

Leu Gln Ser Leu Pro Glu Gly Val Phe Asp Lys Leu Thr Gln Leu Lys
145                 150                 155                 160

Asp Leu Arg Leu Tyr Gln Asn Gln Leu Lys Ser Val Pro Asp Gly Val
                165                 170                 175
```

Phe Asp Arg Leu Thr Ser Leu Gln Tyr Ile Trp Leu His Asp Asn Pro
            180                 185                 190

Trp Asp Cys Thr Cys Pro Gly Ile Arg Tyr Leu Ser Glu Trp Ile Asn
        195                 200                 205

Lys His Ser Gly Val Val Arg Asn Ser Ala Gly Ser Val Ala Pro Asp
    210                 215                 220

Ser Ala Lys Cys Ser Gly Ser Gly Lys Pro Val Arg Ser Ile Ile Cys
225                 230                 235                 240

Pro Thr

<210> SEQ ID NO 7
<211> LENGTH: 242
<212> TYPE: PRT
<213> ORGANISM: Artificial Sequence
<220> FEATURE:
<223> OTHER INFORMATION: Taq Polymerase Repebody r-G6E1A1

<400> SEQUENCE: 7

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Tyr Ile Ala Ala
        35                  40                  45

Ile Asn Ser Asp Ile Lys Ser Val Gln Gly Ile Gln Tyr Leu Pro Asn
    50                  55                  60

Val Arg Arg Leu Lys Leu Gly Ala Asn Lys Leu His Asp Ile Ser Ala
65                  70                  75                  80

Leu Lys Glu Leu Thr Asn Leu Thr Tyr Leu Ser Leu Trp Leu Asn Gln
                85                  90                  95

Leu Gln Ser Leu Pro Asn Gly Val Phe Asp Lys Leu Thr Asn Leu Lys
            100                 105                 110

Glu Leu Ser Leu His Trp Asn Gln Leu Gln Ser Leu Pro Asp Gly Val
        115                 120                 125

Phe Asp Lys Leu Thr Asn Leu Thr Glu Leu Asp Leu Ser Tyr Asn Gln
    130                 135                 140

Leu Gln Ser Leu Pro Glu Gly Val Phe Asp Lys Leu Thr Gln Leu Lys
145                 150                 155                 160

Asp Leu Arg Leu Tyr Gln Asn Gln Leu Lys Ser Val Pro Asp Gly Val
                165                 170                 175

Phe Asp Arg Leu Thr Ser Leu Gln Tyr Ile Trp Leu His Asp Asn Pro
            180                 185                 190

Trp Asp Cys Thr Cys Pro Gly Ile Arg Tyr Leu Ser Glu Trp Ile Asn
        195                 200                 205

Lys His Ser Gly Val Val Arg Asn Ser Ala Gly Ser Val Ala Pro Asp
    210                 215                 220

Ser Ala Lys Cys Ser Gly Ser Gly Lys Pro Val Arg Ser Ile Ile Cys
225                 230                 235                 240

Pro Thr

<210> SEQ ID NO 8
<211> LENGTH: 242
<212> TYPE: PRT
<213> ORGANISM: Artificial Sequence
<220> FEATURE:
<223> OTHER INFORMATION: Taq Polymerase Repebody r-G6E1A8

<400> SEQUENCE: 8

```
Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Ser Val Thr
            20                  25                  30

Asp Ala Val Thr Gln Asn Glu Leu Asn Ser Ile Asp Arg Ile Thr Ala
            35                  40                  45

Met Asn Ser Asp Ile Lys Ser Val Gln Gly Ile Gln Tyr Leu Pro Asn
50                  55                  60

Val Arg Arg Leu Lys Leu Gly Ala Asn Lys Leu His Asp Ile Ser Ala
65                  70                  75                  80

Leu Lys Glu Leu Thr Asn Leu Thr Tyr Leu Ser Leu Trp Leu Asn Gln
                85                  90                  95

Leu Gln Ser Leu Pro Asn Gly Val Phe Asp Lys Leu Thr Asn Leu Lys
            100                 105                 110

Glu Leu Ser Leu His Trp Asn Gln Leu Gln Ser Leu Pro Asp Gly Val
            115                 120                 125

Phe Asp Lys Leu Thr Asn Leu Thr Glu Leu Asp Leu Ser Tyr Asn Gln
130                 135                 140

Leu Gln Ser Leu Pro Glu Gly Val Phe Asp Lys Leu Thr Gln Leu Lys
145                 150                 155                 160

Asp Leu Arg Leu Tyr Gln Asn Gln Leu Lys Ser Val Pro Asp Gly Val
                165                 170                 175

Phe Asp Arg Leu Thr Ser Leu Gln Tyr Ile Trp Leu His Asp Asn Pro
            180                 185                 190

Trp Asp Cys Thr Cys Pro Gly Ile Arg Tyr Leu Ser Glu Trp Ile Asn
            195                 200                 205

Lys His Ser Gly Val Val Arg Asn Ser Ala Gly Ser Val Ala Pro Asp
            210                 215                 220

Ser Ala Lys Cys Ser Gly Ser Gly Lys Pro Val Arg Ser Ile Ile Cys
225                 230                 235                 240

Pro Thr
```

<210> SEQ ID NO 9
<211> LENGTH: 242
<212> TYPE: PRT
<213> ORGANISM: Artificial Sequence
<220> FEATURE:
<223> OTHER INFORMATION: Taq Polymerase Repebody r-G6E1B11

<400> SEQUENCE: 9

```
Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Ser Val Thr
            20                  25                  30

Asp Ala Val Thr Gln Asn Glu Leu Asn Ser Ile Asp Asn Ile Gln Ala
            35                  40                  45

Asn Asn Ser Asp Ile Lys Ser Val Gln Gly Ile Gln Tyr Leu Pro Asn
50                  55                  60

Val Arg Arg Leu Lys Leu Gly Ala Asn Lys Leu His Asp Ile Ser Ala
65                  70                  75                  80

Leu Lys Glu Leu Thr Asn Leu Thr Tyr Leu Ser Leu Trp Leu Asn Gln
                85                  90                  95

Leu Gln Ser Leu Pro Asn Gly Val Phe Asp Lys Leu Thr Asn Leu Lys
            100                 105                 110
```

```
Glu Leu Ser Leu His Trp Asn Gln Leu Gln Ser Leu Pro Asp Gly Val
            115                 120                 125

Phe Asp Lys Leu Thr Asn Leu Thr Glu Leu Asp Leu Ser Tyr Asn Gln
        130                 135                 140

Leu Gln Ser Leu Pro Glu Gly Val Phe Asp Lys Leu Thr Gln Leu Lys
145                 150                 155                 160

Asp Leu Arg Leu Tyr Gln Asn Gln Leu Lys Ser Val Pro Asp Gly Val
                165                 170                 175

Phe Asp Arg Leu Thr Ser Leu Gln Tyr Ile Trp Leu His Asp Asn Pro
            180                 185                 190

Trp Asp Cys Thr Cys Pro Gly Ile Arg Tyr Leu Ser Glu Trp Ile Asn
        195                 200                 205

Lys His Ser Gly Val Val Arg Asn Ser Ala Gly Ser Val Ala Pro Asp
    210                 215                 220

Ser Ala Lys Cys Ser Gly Ser Gly Lys Pro Val Arg Ser Ile Ile Cys
225                 230                 235                 240

Pro Thr

<210> SEQ ID NO 10
<211> LENGTH: 242
<212> TYPE: PRT
<213> ORGANISM: Artificial Sequence
<220> FEATURE:
<223> OTHER INFORMATION: Taq Polymerase Repebody r-G6E1F11

<400> SEQUENCE: 10

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Val Ile Thr Ala
        35                  40                  45

Ile Asn Ser Asp Ile Lys Ser Val Gln Gly Ile Gln Tyr Leu Pro Asn
    50                  55                  60

Val Arg Arg Leu Lys Leu Gly Ala Asn Lys Leu His Asp Ile Ser Ala
65                  70                  75                  80

Leu Lys Glu Leu Thr Asn Leu Thr Tyr Leu Ser Leu Trp Leu Asn Gln
                85                  90                  95

Leu Gln Ser Leu Pro Asn Gly Val Phe Asp Lys Leu Thr Asn Leu Lys
            100                 105                 110

Glu Leu Ser Leu His Trp Asn Gln Leu Gln Ser Leu Pro Asp Gly Val
            115                 120                 125

Phe Asp Lys Leu Thr Asn Leu Thr Glu Leu Asp Leu Ser Tyr Asn Gln
        130                 135                 140

Leu Gln Ser Leu Pro Glu Gly Val Phe Asp Lys Leu Thr Gln Leu Lys
145                 150                 155                 160

Asp Leu Arg Leu Tyr Gln Asn Gln Leu Lys Ser Val Pro Asp Gly Val
                165                 170                 175

Phe Asp Arg Leu Thr Ser Leu Gln Tyr Ile Trp Leu His Asp Asn Pro
            180                 185                 190

Trp Asp Cys Thr Cys Pro Gly Ile Arg Tyr Leu Ser Glu Trp Ile Asn
        195                 200                 205

Lys His Ser Gly Val Val Arg Asn Ser Ala Gly Ser Val Ala Pro Asp
    210                 215                 220
```

Ser Ala Lys Cys Ser Gly Ser Gly Lys Pro Val Arg Ser Ile Ile Cys
225                 230                 235                 240

Pro Thr

<210> SEQ ID NO 11
<211> LENGTH: 242
<212> TYPE: PRT
<213> ORGANISM: Artificial Sequence
<220> FEATURE:
<223> OTHER INFORMATION: Taq Polymerase Repebody r-G6E1H6

<400> SEQUENCE: 11

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Arg Ile Lys Ala
        35                  40                  45

Leu Asn Ser Asp Ile Lys Ser Val Gln Gly Ile Gln Tyr Leu Pro Asn
    50                  55                  60

Val Arg Arg Leu Lys Leu Gly Ala Asn Lys Leu His Asp Ile Ser Ala
65                  70                  75                  80

Leu Lys Glu Leu Thr Asn Leu Thr Tyr Leu Ser Leu Trp Leu Asn Gln
                85                  90                  95

Leu Gln Ser Leu Pro Asn Gly Val Phe Asp Lys Leu Thr Asn Leu Lys
            100                 105                 110

Glu Leu Ser Leu His Trp Asn Gln Leu Gln Ser Leu Pro Asp Gly Val
        115                 120                 125

Phe Asp Lys Leu Thr Asn Leu Thr Glu Leu Asp Leu Ser Tyr Asn Gln
    130                 135                 140

Leu Gln Ser Leu Pro Glu Gly Val Phe Asp Lys Leu Thr Gln Leu Lys
145                 150                 155                 160

Asp Leu Arg Leu Tyr Gln Asn Gln Leu Lys Ser Val Pro Asp Gly Val
                165                 170                 175

Phe Asp Arg Leu Thr Ser Leu Gln Tyr Ile Trp Leu His Asp Asn Pro
            180                 185                 190

Trp Asp Cys Thr Cys Pro Gly Ile Arg Tyr Leu Ser Glu Trp Ile Asn
        195                 200                 205

Lys His Ser Gly Val Val Arg Asn Ser Ala Gly Ser Val Ala Pro Asp
    210                 215                 220

Ser Ala Lys Cys Ser Gly Ser Gly Lys Pro Val Arg Ser Ile Ile Cys
225                 230                 235                 240

Pro Thr

<210> SEQ ID NO 12
<211> LENGTH: 242
<212> TYPE: PRT
<213> ORGANISM: Artificial Sequence
<220> FEATURE:
<223> OTHER INFORMATION: Taq Polymerase Repebody r-G6E1H7

<400> SEQUENCE: 12

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Ser Ile Thr Ala

```
                35                  40                  45
His Asn Ser Asp Ile Lys Ser Val Gln Gly Ile Gln Tyr Leu Pro Asn
 50                  55                  60

Val Arg Arg Leu Lys Leu Gly Ala Asn Lys Leu His Asp Ile Ser Ala
 65                  70                  75                  80

Leu Lys Glu Leu Thr Asn Leu Thr Tyr Leu Ser Leu Trp Leu Asn Gln
                 85                  90                  95

Leu Gln Ser Leu Pro Asn Gly Val Phe Asp Lys Leu Thr Asn Leu Lys
                100                 105                 110

Glu Leu Ser Leu His Trp Asn Gln Leu Gln Ser Leu Pro Asp Gly Val
                115                 120                 125

Phe Asp Lys Leu Thr Asn Leu Thr Glu Leu Asp Leu Ser Tyr Asn Gln
                130                 135                 140

Leu Gln Ser Leu Pro Glu Gly Val Phe Asp Lys Leu Thr Gln Leu Lys
145                 150                 155                 160

Asp Leu Arg Leu Tyr Gln Asn Gln Leu Lys Ser Val Pro Asp Gly Val
                165                 170                 175

Phe Asp Arg Leu Thr Ser Leu Gln Tyr Ile Trp Leu His Asp Asn Pro
                180                 185                 190

Trp Asp Cys Thr Cys Pro Gly Ile Arg Tyr Leu Ser Glu Trp Ile Asn
                195                 200                 205

Lys His Ser Gly Val Val Arg Asn Ser Ala Gly Ser Val Ala Pro Asp
210                 215                 220

Ser Ala Lys Cys Ser Gly Ser Gly Lys Pro Val Arg Ser Ile Ile Cys
225                 230                 235                 240

Pro Thr

<210> SEQ ID NO 13
<211> LENGTH: 242
<212> TYPE: PRT
<213> ORGANISM: Artificial Sequence
<220> FEATURE:
<223> OTHER INFORMATION: Taq Polymerase Repebody r-G6E1H8

<400> SEQUENCE: 13

Glu Thr Ile Thr Val Ser Thr Pro Ile Lys Gln Ile Phe Pro Asp Asp
 1               5                  10                  15

Ala Phe Ala Glu Thr Ile Lys Ala Asn Leu Lys Lys Lys Ser Val Thr
                 20                  25                  30

Asp Ala Val Thr Gln Asn Glu Leu Asn Ser Ile Asp Ser Ile Lys Ala
                 35                  40                  45

Ile Asn Ser Asp Ile Lys Ser Val Gln Gly Ile Gln Tyr Leu Pro Asn
 50                  55                  60

Val Arg Arg Leu Lys Leu Gly Ala Asn Lys Leu His Asp Ile Ser Ala
 65                  70                  75                  80

Leu Lys Glu Leu Thr Asn Leu Thr Tyr Leu Ser Leu Trp Leu Asn Gln
                 85                  90                  95

Leu Gln Ser Leu Pro Asn Gly Val Phe Asp Lys Leu Thr Asn Leu Lys
                100                 105                 110

Glu Leu Ser Leu His Trp Asn Gln Leu Gln Ser Leu Pro Asp Gly Val
                115                 120                 125

Phe Asp Lys Leu Thr Asn Leu Thr Glu Leu Asp Leu Ser Tyr Asn Gln
                130                 135                 140

Leu Gln Ser Leu Pro Glu Gly Val Phe Asp Lys Leu Thr Gln Leu Lys
145                 150                 155                 160
```

-continued

Asp Leu Arg Leu Tyr Gln Asn Gln Leu Lys Ser Val Pro Asp Gly Val
            165                 170                 175
Phe Asp Arg Leu Thr Ser Leu Gln Tyr Ile Trp Leu His Asp Asn Pro
        180                 185                 190
Trp Asp Cys Thr Cys Pro Gly Ile Arg Tyr Leu Ser Glu Trp Ile Asn
            195                 200                 205
Lys His Ser Gly Val Val Arg Asn Ser Ala Gly Ser Val Ala Pro Asp
        210                 215                 220
Ser Ala Lys Cys Ser Gly Ser Gly Lys Pro Val Arg Ser Ile Ile Cys
225                 230                 235                 240
Pro Thr

<210> SEQ ID NO 14
<211> LENGTH: 726
<212> TYPE: DNA
<213> ORGANISM: Artificial Sequence
<220> FEATURE:
<223> OTHER INFORMATION: Taq Polymerase Repebody r-G6

<400> SEQUENCE: 14
gaaaccatta ccgtgagcac cccgatcaaa cagattttc cggatgacgc gttcgccgaa      60
acgatcaaag caaacctgaa gaaaagagc gttaccgatg ctgtcacgca aaatgaactg     120
aacagtattg accagatcat tgcgaataac tccgatatca aatcagtgca aggcattcag     180
tatctgccga atgttcgtta cctggccctg ggtggcaaca aactgcatga catctcggca     240
ctgaaagaac tgaccaatct gacgtatctg tctctgtggc ttaaccaact gcagagcctg     300
ccgaacggcg tgtttgataa actgacgaac ctgaaagaac tgtcgctgca ttggaatcaa     360
ctgcagtctc tgccggatgg tgtgttcgac aaactgacca acctgacgga actggatctg     420
tcctataacc agctgcagtc actgccggaa ggtgttttcg acaaactgac ccagctgaaa     480
gatctgcgcc tgtaccagaa tcagctgaaa tcggtcccgg acggcgtgtt tgatcgtctg     540
accagcctgc agtatatctg gctgcatgat aacccgtggg attgcacctg tccgggtatt     600
cgctacctgt ctgaatggat caataaacac agtggcgttg tccgtaactc cgcgggttca     660
gttgcccccgg attcggcgaa atgctccggc agcggtaaac cggtgcgtag cattatttgc     720
ccgacc                                                                726

<210> SEQ ID NO 15
<211> LENGTH: 726
<212> TYPE: DNA
<213> ORGANISM: Artificial Sequence
<220> FEATURE:
<223> OTHER INFORMATION: Taq Polymerase Repebody r-G6E1

<400> SEQUENCE: 15
gaaaccatta ccgtgagcac cccgatcaaa cagattttc cggatgacgc gttcgccgaa      60
acgatcaaag caaacctgaa gaaaagagc gttaccgatg ctgtcacgca aaatgaactg     120
aacagtattg accagatcat tgcgaataac tccgatatca aatcagtgca aggcattcag     180
tatctgccga atgttcgtcg tctgaagctg ggtgcgaaca aactgcatga catctcggca     240
ctgaaagaac tgaccaatct gacgtatctg tctctgtggc ttaaccaact gcagagcctg     300
ccgaacggcg tgtttgataa actgacgaac ctgaaagaac tgtcgctgca ttggaatcaa     360
ctgcagtctc tgccggatgg tgtgttcgac aaactgacca acctgacgga actggatctg     420
tcctataacc aactgcagtc actgccggaa ggtgttttcg acaaactgac ccagctgaaa     480

| | |
|---|---|
| gatctgcgcc tgtaccagaa tcagctgaaa tcggtcccgg acggcgtgtt tgatcgtctg | 540 |
| accagcctgc agtatatctg gctgcatgat aacccgtggg attgcacctg tccgggtatt | 600 |
| cgctacctgt ctgaatggat caataaacac agtggcgttg tccgtaactc cgcgggttca | 660 |
| gttgccccgg attcggcgaa atgctccggc agcggtaaac cggtgcgtag cattatttgc | 720 |
| ccgacc | 726 |

<210> SEQ ID NO 16
<211> LENGTH: 726
<212> TYPE: DNA
<213> ORGANISM: Artificial Sequence
<220> FEATURE:
<223> OTHER INFORMATION: Taq Polymerase Repebody r-G6E3

<400> SEQUENCE: 16

| | |
|---|---|
| gaaaccatta ccgtgagcac cccgatcaaa cagattttc cggatgacgc gttcgccgaa | 60 |
| acgatcaaag caaacctgaa gaaaagagc gttaccgatg ctgtcacgca aaatgaactg | 120 |
| aacagtattg accagatcat tgcgaataac tccgatatca aatcagtgca aggcattcag | 180 |
| tatctgccga atgttcgtaa gctgaagctg ggtgctaaca aactgcatga catctcggca | 240 |
| ctgaaagaac tgaccaatct gacgtatctg tctctgtggc ttaaccaact gcagagcctg | 300 |
| ccgaacggcg tgtttgataa actgacgaac ctgaaagaac tgtcgctgca ttggaatcaa | 360 |
| ctgcagtctc tgccggatgg tgtgttcgac aaactgacca acctgacgga actggatctg | 420 |
| tcctataacc aactgcagtc actgccggaa ggtgttttcg acaaactgac ccagctgaaa | 480 |
| gatctgcgcc tgtaccagaa tcagctgaaa tcggtcccgg acggcgtgtt tgatcgtctg | 540 |
| accagcctgc agtatatctg gctgcatgat aacccgtggg attgcacctg tccgggtatt | 600 |
| cgctacctgt ctgaatggat caataaacac agtggcgttg tccgtaactc cgcgggttca | 660 |
| gttgccccgg attcggcgaa atgctccggc agcggtaaac cggtgcgtag cattatttgc | 720 |
| ccgacc | 726 |

<210> SEQ ID NO 17
<211> LENGTH: 726
<212> TYPE: DNA
<213> ORGANISM: Artificial Sequence
<220> FEATURE:
<223> OTHER INFORMATION: Taq Polymerase Repebody r-G6D9

<400> SEQUENCE: 17

| | |
|---|---|
| gaaaccatta ccgtgagcac cccgatcaaa cagattttc cggatgacgc gttcgccgaa | 60 |
| acgatcaaag caaacctgaa gaaaagagc gttaccgatg ctgtcacgca aaatgaactg | 120 |
| aacagtattg accagatcat tgcgaataac tccgatatca aatcagtgca aggcattcag | 180 |
| tatctgccga atgttcgtgc tctgaagctg ggggcgaaca aactgcatga catctcggca | 240 |
| ctgaaagaac tgaccaatct gacgtatctg tctctgtggc ttaaccaact gcagagcctg | 300 |
| ccgaacggcg tgtttgataa actgacgaac ctgaaagaac tgtcgctgca ttggaatcaa | 360 |
| ctgcagtctc tgccggatgg tgtgttcgac aaactgacca acctgacgga actggatctg | 420 |
| tcctataacc aactgcagtc actgccggaa ggtgttttcg acaaactgac ccagctgaaa | 480 |
| gatctgcgcc tgtaccagaa tcagctgaaa tcggtcccgg acggcgtgtt tgatcgtctg | 540 |
| accagcctgc agtatatctg gctgcatgat aacccgtggg attgcacctg tccgggtatt | 600 |
| cgctacctgt ctgaatggat caataaacac agtggcgttg tccgtaactc cgcgggttca | 660 |

```
gttgccccgg attcggcgaa atgctccggc agcggtaaac cggtgcgtag cattatttgc    720
ccgacc                                                               726
```

<210> SEQ ID NO 18
<211> LENGTH: 726
<212> TYPE: DNA
<213> ORGANISM: Artificial Sequence
<220> FEATURE:
<223> OTHER INFORMATION: Taq Polymerase Repebody r-G6E1A1

<400> SEQUENCE: 18

```
gaaaccatta ccgtgagcac cccgatcaaa cagattttc cggatgacgc gttcgccgaa     60
acgatcaaag caaacctgaa gaaaaagagc gttaccgatg ctgtcacgca aaatgaactg    120
aacagtattg actatatcgc ggcgattaat tccgatatca aatcagtgca aggcattcag    180
tatctgccga atgttcgtcg tctgaagctg ggtgcgaaca aactgcatga catctcggca    240
ctgaaagaac tgaccaatct gacgtatctg tctctgtggc ttaaccaact gcagagcctg    300
ccgaacggcg tgtttgataa actgacgaac ctgaaagaac tgtcgctgca ttggaatcaa    360
ctgcagtctc tgccggatgg tgtgttcgac aaactgacca acctgacgga actggatctg    420
tcctataacc aactgcagtc actgccggaa ggtgttttcg acaaactgac ccagctgaaa    480
gatctgcgcc tgtaccagaa tcagctgaaa tcggtcccgg acggcgtgtt tgatcgtctg    540
accagcctgc agtatatctg gctgcatgat aacccgtggg attgcacctg tccgggtatt    600
cgctacctgt ctgaatggat caataaacac agtggcgttg tccgtaactc cgcgggttca    660
gttgccccgg attcggcgaa atgctccggc agcggtaaac cggtgcgtag cattatttgc    720
ccgacc                                                               726
```

<210> SEQ ID NO 19
<211> LENGTH: 726
<212> TYPE: DNA
<213> ORGANISM: Artificial Sequence
<220> FEATURE:
<223> OTHER INFORMATION: Taq Polymerase Repebody r-G6E1A8

<400> SEQUENCE: 19

```
gaaaccatta ccgtgagcac cccgatcaaa cagattttc cggatgacgc gttcgccgaa     60
acgatcaaag caaacctgaa gaaaaagagc gttaccgatg ctgtcacgca aaatgaactg    120
aacagtattg acaggatcac ggcgatgaat tccgatatca aatcagtgca aggcattcag    180
tatctgccga atgttcgtcg tctgaagctg ggtgcgaaca aactgcatga catctcggca    240
ctgaaagaac tgaccaatct gacgtatctg tctctgtggc ttaaccaact gcagagcctg    300
ccgaacggcg tgtttgataa actgacgaac ctgaaagaac tgtcgctgca ttggaatcaa    360
ctgcagtctc tgccggatgg tgtgttcgac aaactgacca acctgacgga actggatctg    420
tcctataacc aactgcagtc actgccggaa ggtgttttcg acaaactgac ccagctgaaa    480
gatctgcgcc tgtaccagaa tcagctgaaa tcggtcccgg acggcgtgtt tgatcgtctg    540
accagcctgc agtatatctg gctgcatgat aacccgtggg attgcacctg tccgggtatt    600
cgctacctgt ctgaatggat caataaacac agtggcgttg tccgtaactc cgcgggttca    660
gttgccccgg attcggcgaa atgctccggc agcggtaaac cggtgcgtag cattatttgc    720
ccgacc                                                               726
```

<210> SEQ ID NO 20
<211> LENGTH: 726

```
<212> TYPE: DNA
<213> ORGANISM: Artificial Sequence
<220> FEATURE:
<223> OTHER INFORMATION: Taq Polymerase Repebody r-G6E1B11

<400> SEQUENCE: 20
gaaaccatta ccgtgagcac cccgatcaaa cagattttc cggatgacgc gttcgccgaa      60
acgatcaaag caaacctgaa gaaaagagc gttaccgatg ctgtcacgca aaatgaactg     120
aacagtattg acaatatcca ggcgaataat tccgatatca aatcagtgca aggcattcag     180
tatctgccga atgttcgtcg tctgaagctg ggtgcgaaca aactgcatga catctcggca     240
ctgaaagaac tgaccaatct gacgtatctg tctctgtggc ttaaccaact gcagagcctg     300
ccgaacggcg tgtttgataa actgacgaac ctgaaagaac tgtcgctgca ttggaatcaa     360
ctgcagtctc tgccggatgg tgtgttcgac aaactgacca acctgacgga actggatctg     420
tcctataacc aactgcagtc actgccggaa ggtgttttcg acaaactgac ccagctgaaa     480
gatctgcgcc tgtaccagaa tcagctgaaa tcggtcccgg acggcgtgtt tgatcgtctg     540
accagcctgc agtatatctg gctgcatgat aacccgtggg attgcacctg tccgggtatt     600
cgctacctgt ctgaatggat caataaacac agtggcgttg tccgtaactc cgcgggttca     660
gttgccccgg attcggcgaa atgctccggc agcggtaaac cggtgcgtag cattatttgc     720
ccgacc                                                                  726

<210> SEQ ID NO 21
<211> LENGTH: 726
<212> TYPE: DNA
<213> ORGANISM: Artificial Sequence
<220> FEATURE:
<223> OTHER INFORMATION: Taq Polymerase Repebody r-G6E1F11

<400> SEQUENCE: 21
gaaaccatta ccgtgagcac cccgatcaaa cagattttc cggatgacgc gttcgccgaa      60
acgatcaaag caaacctgaa gaaaagagc gttaccgatg ctgtcacgca aaatgaactg     120
aacagtattg acgttatcac ggcgattaat tccgatatca aatcagtgca aggcattcag     180
tatctgccga atgttcgtcg tctgaagctg ggtgcgaaca aactgcatga catctcggca     240
ctgaaagaac tgaccaatct gacgtatctg tctctgtggc ttaaccaact gcagagcctg     300
ccgaacggcg tgtttgataa actgacgaac ctgaaagaac tgtcgctgca ttggaatcaa     360
ctgcagtctc tgccggatgg tgtgttcgac aaactgacca acctgacgga actggatctg     420
tcctataacc aactgcagtc actgccggaa ggtgttttcg acaaactgac ccagctgaaa     480
gatctgcgcc tgtaccagaa tcagctgaaa tcggtcccgg acggcgtgtt tgatcgtctg     540
accagcctgc agtatatctg gctgcatgat aacccgtggg attgcacctg tccgggtatt     600
cgctacctgt ctgaatggat caataaacac agtggcgttg tccgtaactc cgcgggttca     660
gttgccccgg attcggcgaa atgctccggc agcggtaaac cggtgcgtag cattatttgc     720
ccgacc                                                                  726

<210> SEQ ID NO 22
<211> LENGTH: 726
<212> TYPE: DNA
<213> ORGANISM: Artificial Sequence
<220> FEATURE:
<223> OTHER INFORMATION: Taq Polymerase Repebody r-G6E1H6

<400> SEQUENCE: 22
```

```
gaaaccatta ccgtgagcac cccgatcaaa cagattttc cggatgacgc gttcgccgaa      60
acgatcaaag caaacctgaa gaaaaagagc gttaccgatg ctgtcacgca aaatgaactg    120
aacagtattg accgtatcaa ggcgctgaat tccgatatca aatcagtgca aggcattcag    180
tatctgccga atgttcgtcg tctgaagctg ggtgcgaaca aactgcatga catctcggca    240
ctgaaagaac tgaccaatct gacgtatctg tctctgtggc ttaaccaact gcagagcctg    300
ccgaacggcg tgtttgataa actgacgaac ctgaaagaac tgtcgctgca ttggaatcaa    360
ctgcagtctc tgccggatgg tgtgttcgac aaactgacca acctgacgga actggatctg    420
tcctataacc aactgcagtc actgccggaa ggtgttttcg acaaactgac ccagctgaaa    480
gatctgcgcc tgtaccagaa tcagctgaaa tcggtcccgg acggcgtgtt tgatcgtctg    540
accagcctgc agtatatctg gctgcatgat aacccgtggg attgcacctg tccgggtatt    600
cgctacctgt ctgaatggat caataaacac agtggcgttg tccgtaactc cgcgggttca    660
gttgccccgg attcggcgaa atgctccggc agcggtaaac cggtgcgtag cattatttgc    720
ccgacc                                                                726
```

<210> SEQ ID NO 23  
<211> LENGTH: 726  
<212> TYPE: DNA  
<213> ORGANISM: Artificial Sequence  
<220> FEATURE:  
<223> OTHER INFORMATION: Taq Polymerase Repebody r-G6E1H7

<400> SEQUENCE: 23

```
gaaaccatta ccgtgagcac cccgatcaaa cagattttc cggatgacgc gttcgccgaa      60
acgatcaaag caaacctgaa gaaaaagagc gttaccgatg ctgtcacgca aaatgaactg    120
aacagtattg acagtatcac ggcgcataat tccgatatca aatcagtgca aggcattcag    180
tatctgccga atgttcgtcg tctgaagctg ggtgcgaaca aactgcatga catctcggca    240
ctgaaagaac tgaccaatct gacgtatctg tctctgtggc ttaaccaact gcagagcctg    300
ccgaacggcg tgtttgataa actgacgaac ctgaaagaac tgtcgctgca ttggaatcaa    360
ctgcagtctc tgccggatgg tgtgttcgac aaactgacca acctgacgga actggatctg    420
tcctataacc aactgcagtc actgccggaa ggtgttttcg acaaactgac ccagctgaaa    480
gatctgcgcc tgtaccagaa tcagctgaaa tcggtcccgg acggcgtgtt tgatcgtctg    540
accagcctgc agtatatctg gctgcatgat aacccgtggg attgcacctg tccgggtatt    600
cgctacctgt ctgaatggat caataaacac agtggcgttg tccgtaactc cgcgggttca    660
gttgccccgg attcggcgaa atgctccggc agcggtaaac cggtgcgtag cattatttgc    720
ccgacc                                                                726
```

<210> SEQ ID NO 24  
<211> LENGTH: 726  
<212> TYPE: DNA  
<213> ORGANISM: Artificial Sequence  
<220> FEATURE:  
<223> OTHER INFORMATION: Taq Polymerase Repebody r-G6E1H8

<400> SEQUENCE: 24

```
gaaaccatta ccgtgagcac cccgatcaaa cagattttc cggatgacgc gttcgccgaa      60
acgatcaaag caaacctgaa gaaaaagagc gttaccgatg ctgtcacgca aaatgaactg    120
aacagtattg acagtatcaa ggcgattaat tccgatatca aatcagtgca aggcattcag    180
tatctgccga atgttcgtcg tctgaagctg ggtgcgaaca aactgcatga catctcggca    240
```

-continued

```
ctgaaagaac tgaccaatct gacgtatctg tctctgtggc ttaaccaact gcagagcctg      300
ccgaacggcg tgtttgataa actgacgaac ctgaaagaac tgtcgctgca ttggaatcaa      360
ctgcagtctc tgccggatgg tgtgttcgac aaactgacca acctgacgga actggatctg      420
tcctataacc aactgcagtc actgccggaa ggtgttttcg acaaactgac ccagctgaaa      480
gatctgcgcc tgtaccagaa tcagctgaaa tcggtcccgg acggcgtgtt tgatcgtctg      540
accagcctgc agtatatctg gctgcatgat aacccgtggg attgcacctg tccgggtatt      600
cgctacctgt ctgaatggat caataaacac agtggcgttg tccgtaactc cgcgggttca      660
gttgccccgg attcggcgaa atgctccggc agcggtaaac cggtgcgtag cattatttgc      720
ccgacc                                                                 726
```

<210> SEQ ID NO 25
<211> LENGTH: 726
<212> TYPE: DNA
<213> ORGANISM: Artificial Sequence
<220> FEATURE:
<223> OTHER INFORMATION: Repebody-VLR4
<220> FEATURE:
<221> NAME/KEY: misc_binding
<222> LOCATION: (271)..(354)
<223> OTHER INFORMATION: N=A+G+C+T, K=G+T

<400> SEQUENCE: 25

```
gaaaccatta ccgtgagcac cccgatcaaa cagatttttc cggatgacgc gttcgccgaa       60
acgatcaaag caaacctgaa gaaaaagagc gttaccgatg ctgtcacgca aaatgaactg      120
aacagtattg accagatcat tgcgaataac tccgatatca aatcagtgca aggcattcag      180
tatctgccga atgttcgtta cctggccctg ggtggcaaca aactgcatga catctcggca      240
ctgaaagaac tgaccaatct gacgtatctg nnkctgnnkn nkaaccaact gcagagcctg      300
ccgaacggcg tgtttgataa actgacgaac ctgaaagaac tgnnkctgnn knnkaatcaa      360
ctgcagtctc tgccggatgg tgtgttcgac aaactgacca acctgacgga actggatctg      420
tcctataacc aactgcagtc actgccggaa ggtgttttcg acaaactgac ccagctgaaa      480
gatctgcgcc tgtaccagaa tcagctgaaa tcggtcccgg acggcgtgtt tgatcgtctg      540
accagcctgc agtatatctg gctgcatgat aacccgtggg attgcacctg tccgggtatt      600
cgctacctgt ctgaatggat caataaacac agtggcgttg tccgtaactc cgcgggttca      660
gttgccccgg attcggcgaa atgctccggc agcggtaaac cggtgcgtag cattatttgc      720
ccgacc                                                                 726
```

POLYPEPTIDE SPECIFICALLY BINDING TO TAQ DNA POLYMERASE AND USE THEREOF

SEQUENCE LISTING

The Sequence Listing submitted in text format (.txt) filed on Nov. 21, 2017, named "SequenceListing.txt", created on Nov. 20, 2017, 39.0 KB, is incorporated herein by reference.

TECHNICAL FIELD

The present invention relates to the field of nucleic acid amplification technology.

BACKGROUND ART

PCR (Polymerase Chain Reaction) is a method for amplifying certain nucleic acid, which is mostly widely used in the biological, biochemical and medical fields (Yamamoto, Y. *Clin. Diagn. Lab. Immunol.* 2002, 9 (3), 508-514). PCR consists of a plurality of multiple cycles, each consisting of three steps (denaturation, primer annealing and extension), in which each of the steps is performed at a suitable temperature. An enzyme that is mostly widely used in PCR is *Therms aquaticus* Taq DNA polymerase which is thermally stable at high temperatures, and thus makes it possible to perform PCR in an efficient and stable manner.

However, the Taq DNA polymerase has a disadvantage in that, if primers bind to template nucleic acid before completion of the denaturation step of PCR due to their activity at room temperature or if a dimer is formed between primers, the Taq DNA polymerase enables this template to be nonspecifically amplified, thus greatly reducing the efficiency and accuracy of gene amplification.

To prevent undesired amplification of nucleic acids, hot-start PCR technology was developed to keep the Taq DNA polymerase in a deactivated state before reaching a certain temperature or to inhibit the extension of primers (Paul, N.; Shum, J.; Le, T. *Methods Mol. Biol.* 2010, 630, 301-318).

Previously, a technology was used in which components other than polymerase, required for PCR, are preheated to a melting temperature of 95° C., followed by addition of polymerase; however, this technology had a problem in that the additional treatment causes inconvenience (D'Aquila, R. T.; Bechtel, L. J.; Videler, J. a; Eron, J. J.; Gorczyca, P.; Kaplan, J. C. *Nucleic Acids Res.* 1991, 19 (13), 3749). Another method is a technology in which wax or beads are used to physically isolate polymerase before PCR reaction. However, this technology also had problems in that the additional treatment procedure and the re-solidification of wax result in inconvenience and reduce the efficiency of PCR reaction (Hebert, B.; Bergeron, J.; Potworowski, E. F.; Tijssen, P. *Molecular and cellular probes.* 1993, pp 249-252). Thereafter, a technology that chemically inhibits Taq DNA polymerase activity was developed, but had problems in that the preparation process is complex and a time period of 10 minutes or more is required for polymerase reactivation, resulting in DNA cleavage (Moretti, T.; Koons, B.; Budowle, B. *Biotechniques* 1998, 25 (4), 716-722.). In addition, a technology of inactivating Taq DNA polymerase by antibody was developed. An immunoglobulin-based antibody that specifically recognizes Taq DNA polymerase binds to polymerase at low temperature to inhibit the polymerase activity, and is separated from the polymerase at increased temperature during PCR, resulting in activation of the polymerase (Scalice, E. R.; Sharkey, D. J.; Daiss, J. L. *J. Immunol. Methods* 1994, 172 (2), 147-163). This neutralizing antibody provides a convenient and highly effective method, but has problems in that it is produced by a costly and complex process and forms an aggregate due to its high molecular weight.

Korean Patent No. 1488110 relates to the preparation of mutant Neq HS DNA polymerase derived from *Nanoarchaeum equitans* and the application thereof for hot-start PCR, and discloses hot-start PCR based on trans-splicing that occurs at high temperature.

However, there are still needs to develop a new methods capable of overcoming problems encountered in the conventional methods as well as capable of binding to Taq DNA polymerase to neutralize the polymerase activity.

DISCLOSURE

Technical Problem

The present invention is intended to provide a technology capable of increasing the efficiency and accuracy of nucleic acid amplification by using a polypeptide, which binds to Taq DNA polymerase, to effectively inhibit nonspecific amplification that may occur in PCR performed using Taq DNA polymerase.

Technical Solution

In one aspect, the present invention provides a polypeptide binding specifically to Taq DNA polymerase, in which the polypeptide comprises a fusion of N-terminus of intemalin B protein, a modified repeat module of variable lymphocyte receptor (VLR) protein, and C-terminus of the VLR protein, and is represented by an amino acid sequence of SEQ ID NO: 1 wherein residue 45 is Q, S, R, Y, V or N; residue 47 is I, T, K, A or Q; residue 49 is N, H, L, M or I; residue 67 is Y, R, A or K; residue 69 is A or K; residue 72 is G or A; residue 91 is I or S; residue 93 is T or W; residue 94 is G or L; residue 115 is V or S; residue 117 is V or H; and residue 118 is E or W.

In one embodiment of the present invention, the polypeptide is represented by the amino acid sequence of SEQ ID NO:1 wherein the residues mutated in the first round, residues 91 is S; 93 is W; 94 is L; 115 is S; 117 is H; and 118 is W, and the residue 67 is Y, R, A or K; residue 69 is A or K; residue 72 is G or A from the second round; and residue 45 is Q, S, R, Y, V or N; residue 47 is I, T, K, A or Q; residue 49 is N, H, L, M or I from the third round. In other embodiment, the polypeptide is represented by the amino acid sequence of SEQ ID NO:1 wherein the residue 91 is S; 93 is W; 94 is L; 115 is S; 117 is H; and 118 is W, and the residues mutated at the second round, 67 is R, A or K; residue 69 is K; residue 72 is A; and residue 45 is Q, S, R, Y, V or N; residue 47 is I, T, K, A or Q; residue 49 is N, H, L, M or I. In still other embodiment, the polypeptide is represented by the amino acid sequence of SEQ ID NO:1 wherein residue 91 is S; 93 is W; 94 is L; 115 is S; 117 is H; and 118 is W, and residue 67 is R, A or K; residue 69 is K; residue 72 is A; and residue 45 is S, R, Y, V or N; residue 47 is T, K, A or Q; residue 49 is H, L, M or I.

In one embodiment of the present invention, the polypeptide binding specifically to Taq DNA polymerase is represented by the amino acid sequence of SEQ ID NO: 1 wherein residue 45 is Q, S, R, Y, V or N; residue 47 is I, T, K, A or Q; residue 49 is N, H, L, M or I; residue 67 is Y, R, A or K; residue 69 is A or K; residue 72 is G or A; residue 91 is S; residue 93 is W; residue 94 is L; residue 115 is S; residue 117 is H; and residue 118 is W.

In another embodiment, the polypeptide binding specifically to Taq DNA polymerase according to the present invention is represented by the amino acid sequence of SEQ ID NO: 1 wherein residue 45 is Q, S, R, Y, V or N; residue 47 is I, T, K, A or Q; residue 49 is N, H, L, M or I; residue 67 is R; residue 69 is K; residue 72 is A; residue 91 is S; residue 93 is W; residue 94 is L; residue 115 is S; residue 117 is H; and residue 118 is W.

In still other embodiment, the polypeptide according to the present invention has an amino acid sequence represented by any one of SEQ ID NO: 3 to 13 or an amino acid sequence wherein one or more of residues 45, 47, 49, 67, 69, 72, 91, 93, 94, 115, 117 and 118 in the amino acid sequence of any one of SEQ ID NO: 3 to 13 are substituted with highly conservative or conservative residues as shown in Table 1 below.

In another aspect, the present invention provides a polypeptide having an amino acid sequence represented by SEQ ID NO: 13 or an amino acid sequence with conserved substitutions at least one of the following residues in the amino acid sequence of SEQ ID NO: 13: S, T, A or N at residue 45; K, R, Q, E or N at residue 47; A, S, G or T at residue 48; I, L, V, M, or F at residue 49; R, K, Q or H at residue 67; K, R, Q, E or N at residue 69; A, S, G or T at residue 72; S, T, A or N at residue 91; W, Y or F at residue 93; L, I, V, M or F at residue 94; S, T, A or N at residue 115; H, N, Q, R or Y at residue 117; and W, Y or F at residue 118.

In one embodiment, the polypeptide binding specifically to Taq DNA polymerase according to the present invention is present as a homo- or hetero-dimer or a homo- or hetero-trimer.

In another aspect, the present invention also provides a polynucleotide encoding the polypeptide according to the present invention. In one embodiment the polynucleotide sequence encoding SEQ ID NO: 3 to 13 is represented by SEQ ID NO: 14 to 24, respectively.

In still another aspect, the present invention also provides a recombinant vector comprising the polynucleotide according to the present invention, or a transformed cell having the vector introduced therein.

The present invention also provides a use of one or more polypeptides, disclosed herein, for hot-start PCR.

The present invention also provides a use of one or more polypeptides, disclosed herein, in preparation of a hot-start PCR composition.

In yet another aspect, the present invention also provides a hot-start PCR composition or kit comprising the polypeptides according to the present invention, or a hot-start PCR method performed using the polypeptides according to the present invention.

Advantageous Effects

The polypeptide according to the present invention can be conveniently prepared as well as bind to Taq DNA polymerase with high affinity to inhibit the polymerase activity before the start of PCR. Furthermore, when a PCR reaction reaches a temperature of 95° C. during the denaturation step, the present polypeptide can be effectively separated from the Taq DNA polymerase for amplification. Thus, the polypeptide according to the present invention can prevent non-specific amplification at low temperatures before the start of PCR, making it possible to perform a highly specific PCR reaction in a cost-effective and highly efficient manner.

DESCRIPTION OF DRAWINGS

FIG. 1 illustrates the exemplary structure of repebody-VLR4 used to screen the polypeptide according to the present invention, and shows modules into which the mutations are introduced for screening. A total of three libraries was consecutively constructed in which a r-G6 clone showing the highest binding affinity in the first round was used as a template for library construction in the second round, and a r-G6E1 clone showing the highest binding affinity in the second screening round was used as a template for library construction in the third round. In the first library, a mutation was introduced into the concave region of LRRV2 and LRRV3 (yellow), and in the second library, a mutation was introduced into LRRV1 (green), and in the third library, a mutation was introduced into LRR1 (blue). The name of each clone screened using each library in each round is shown at the lower part of the figure.

FIG. 2 shows the results of ELISA performed to determine the affinity of the clone r-G6 to Taq DNA polymerase selected in the first round as shown in FIG. 1 The results show that the clone r-G6 did not bind to BSA, but did bind specifically to Taq DNA polymerase. Herein, it has been shown the ELISA signal of Taq DNA polymerase was decreased when the competitor antibody added (JumpStart antibody; Sigma Aldrich) which binds to Taq DNA polymerase and inhibit its activity, indicating that the clone r-G6 has an epitope similar to that of the antibody.

FIG. 3 shows changes in the amino acid sequences of all clones obtained by performing phage display biopanning in each round by use of the libraries constructed as shown in FIG. 1, and also shows the results of measuring the dissociation constants of the clones by an isothermal titration calorimeter (ITC). The r-G6 clone showing the highest binding affinity in the first round was used as a template for library construction in the second round, and the r-G6E1 clone showing the highest binding affinity in the second screening round was used as a template for library construction in the third round.

FIG. 4 shows the results of phage ELISA analysis performed to analyze the Taq DNA polymerase binding specificity of an r-G6E1H8 clone selected in the third round.

FIG. 5 shows the results of circular dichroism (CD) analysis performed to measure the protein melting temperature of repebody clones selected in each round.

FIG. 6 shows the results of analyzing inhibitory effects of the present repebody clones selected in each round on the Taq DNA polymerase activity.

FIG. 7 shows experimental results indicating that Taq DNA polymerase inactivated by the r-G6E1H8 repebody clone selected in the third round was rapidly reactivated. In this experiment, conventional antibody and chemically modified Taq DNA polymerase were used as comparative controls.

FIG. 8 shows the results of block PCR performed to evaluate the hot-start PCR effects of the repebody clones of the present invention.

FIG. 9 shows the results of real-time PCR performed to evaluate the hot-start PCR effects of repebody clones of the present invention.

FIG. 10 shows the results of analyzing inhibitory effect of a repebody dimer according to the present invention on the Taq DNA polymerase activity.

MODE FOR INVENTION

The present inventors have successfully developed polypeptides, non-antibody protein scaffolds that bind specifically to Taq polymerase and are capable of replacing conventional antibodies used in hot-start PCR.

The polypeptide according to the present invention is referred to as "repebody", which is a fused polypeptide of the N-terminus of internalin B protein, a modified leucine-rich repeat (LRR) module of variable lymphocyte receptor (VRL) protein, and the C-terminus of the VRL protein. The repebody based on its structure can be divided into a concave region and a convex region. Here, the concave region has a high sequence variety and is important for protein-protein interaction, and the convex region contains highly conserved sequences and serves to stably maintain the structure or framework of the repebody. The repebody comprises a plurality of modules, and the modules may be divided, according to the consensus sequence found in LRR moudule into LRR1, LRRV1, LRRV2, LRRV3, LRRV4, LRRV5, and LRRVe. One or more modules may be omitted. For a detailed description for producing the repebody and the structure of the repebody, references may be made to Korean Patent No. 1356076 and Korean Patent No. 1517196.

The repebody has a size of about ⅕ of antibody, and can be produced in large quantities from *E. coli,* and shows little or no immunogenicity in animal studies. In addition, the repebody has very high thermal and pH stabilities, and its ability to bind to a target can be increased to picomole levels, and its specificity for a target is very high. Thus, the repebody is a very useful alternative to antibody.

Particularly, the "LRR (leucine rich repeat) module" contained in the repebody consists of 20 to 30 amino acids in which leucine is repeated at a certain position, and has a repeating sequence pattern of "LxxLxxLxLxxN", wherein L is a hydrophobic amino acids such as alanine, glycine, phenylalanine, tyrosine, leucine, isoleucine, valine, and tryptophan; N is asparagine, glutamine, serine, cysteine or threonine; and x is any amino acid.

In the present invention, as shown in FIG. 1, a mutation was sequentially introduced into certain amino acids in the LRR module from LRRV in consideration of the repebody structure, thereby sequentially constructing mutant libraries having increasing binding affinities. From the libraries, non-antibody scaffold polypeptides capable of binding specifically to Taq DNA polymerase to effectively inhibit the polymerase activity were selected.

The polypeptide according to the present invention is a heat-stable Taq DNA polymerase inhibitor capable of binding to Taq DNA polymerase at low temperatures, and capable of separating therefrom at a denaturation temperature. The low temperature is a temperature before the initial denaturation of a PCR reaction starts, or a temperature at which nonspecific primer annealing and the resulting DNA synthesis may occur. The range of low temperature may vary depending on conditions such as specific primers used in the reaction and for example includes 50 to 60° C., or 50° C. or below. By such binding activity at low temperature and separation therefrom at the denaturation temperature thus reactivating the Taq DNA polymerase, the nonspecific polymerization by Taq Polymerase can be effectively prevented.

In the present invention, in order to identify a more efficient repebody, the melting temperature of a repebody used as a template for library construction was reduced. To this end, among the modules contained in the conventional repebody as described in the above-mentioned patent documents, particularly the LRRV4 module was removed. The number of modules in the repebody influences the thermal stability of the repebody. In order to develop a Taq DNA polymerase inhibitor having a thermal stability suitable for the purpose of the present invention, a repebody lacking one module was used as a template to construct a library. A library was constructed from the concave region of a repebody, and a repebody binding specifically to a target substance was selected. In this manner, sequential screening was performed, thereby optimizing the interaction between residues present at the interface between a repebody and a target substance, thereby increasing the binding affinity of the repebody for the target substance.

In addition, in the present invention, mutations were sequentially introduced in three rounds in order to further increase the binding affinity. Specifically, a clone showing the highest binding affinity in the first round was used to construct a second library in the second round, and a clone showing the highest binding affinity in the second selection round was used to construct a third library in the third round. By this sequential screening from LRRV3 and LRRV2, to LRRV1 and to LRR1, the affinity is increased as with screenings. Thus as long as the sequence or mutations selected at the first round is included, other mutations selected at the next round can be included in various combinations.

In the present invention, in the first round, mutagenesis was performed at residues 91, 93, 94, 115, 117 and 118 of SEQ ID NO: 1 which represents the concave region LRRV2 and LRRV3, and a polypeptide binding specifically to Taq polymerase was selected. Using the selected polypeptide at the first round, second mutagenesis was performed sequentially at residues 67, 69, 71 and 72 in the concave region LRRV1 and the LRR1, and third mutagenesis was performed at residues 45, 47, 49 and 50, thereby selecting a polypeptide having increased binding affinity to Taq polymerase.

Therefore, in one aspect, the present invention is directed to a polypeptide binding specifically to a Taq DNA polymerase, which is a fused polypeptide of the N-terminus of internalin B protein, a modified repeat module of variable lymphocyte receptor (VLR) protein, and the C-terminus of the VLR protein, and is represented by an amino acid sequence of SEQ ID NO: 1 wherein the residues selected at the first rounds, i.e., residue 91 is S; 93 is W; 94 is L; 115 is S; 117 is H; and 118 is W, and the residues selected at the second round i.e., residue 67 is Y, R, A or K; residue 69 is A or K; residue 72 is G or A; and the residues selected at the third round i.e., residue 45 is Q, S, R, Y, V or N; residue 47 is I, T, K, A or Q; residue 49 is N, H, L, M or I. In other embodiment, the polypeptide is represented by the amino acid sequence of SEQ ID NO:1 wherein residue 91 is S; 93 is W; 94 is L; 115 is S; 117 is H; and 118 is W, and residue 67 is R, A or K; residue 69 is K; residue 72 is A; and residue 45 is Q, S, R, Y, V or N; residue 47 is I, T, K, A or Q; residue 49 is N, H, L, M or I. In still other embodiment, the polypeptide is represented by the amino acid sequence of SEQ ID NO:1 wherein residue 91 is S; 93 is W; 94 is L; 115 is S; 117 is H; and 118 is W, and residue 67 is R, A or K; residue 69 is K; residue 72 is A; and residue 45 is S, R, Y, V or N; residue 47 is T, K, A or Q; residue 49 is H, L, M or I.

As used herein, the term "Taq DNA polymerase" is meant to include an enzyme derived from Therms aquaticus, a thermophilic bacterium, or derivatives or variants thereof having an equivalent activity. Taq DNA polymerase is commercially available from various companies. Mutated Taq DNA polymerases of various types and/or origins fall within the definition of Taq DNA polymerase in the present invention, as long as the polypeptide according to the present invention is capable of binding thereto.

As described above, the number of mutations introduced into the polypeptide of the present invention and the binding affinity of the polypeptide increase as the number of selection rounds increases. However, since a polypeptide is selected based on its binding affinity for Taq polymerase in each round, the scope of the present invention encompasses not only a mutant polypeptide selected in the third round, but also mutant polypeptides selected in the first and second rounds.

In addition, introduction of mutations at the above-described residue positions in each selection round was performed in a sequential manner. Thus the repebody of the present invention may or may not include mutations at all the residues described herein. A mutant repebody selected in each round also falls within the scope of the present invention. Furthermore, a polypeptide containing a mutation at one or more of the above-described positions falls within the scope of the present invention, as long as it has binding affinity for Taq DNA polymerase.

The residues or positions to be mutated for the present purpose in the present invention are selected by efforts that are not obvious to those skilled in the art. Specifically, in the first selection round, mutagenesis was performed at residue positions corresponding to the center of a concave region among the residues of LRRV2 and LRRV3 modules of repebody, and a repebody (G6) was selected and used as a template for the next round of selection. In the next selection round, mutations were introduced into both sides of each of the two modules of the first library to increase binding affinity. However, the mutations were not introduced in the module region corresponding to the C-terminus. Thus, in order to select a repebody binding to Taq DNA polymerase, a second library was applied to LRRV1 which is the N-terminal module of LRRV2, thereby identifying a clone (G6E1) having increased binding affinity, and then a third library was applied to LRR1, thereby identifying a clone (G6E1H8) having further increased binding affinity.

Particularly, a polypeptide showing the highest binding affinity in the first selection round was used in the second selection round, and a polypeptide containing a mutation at one or more of the residues used in mutagenesis in the second round falls within the scope of the present invention. Likewise, a polypeptide showing the highest binding affinity in the second selection round was used in the third selection round, and a polypeptide containing a mutation at one or more of the residues used in mutagenesis in the third round falls within the scope of the present invention.

Therefore, in another aspect, the present invention is directed to a polypeptide binding specifically to Taq DNA polymerase and having the following sequence, in which the polypeptide was selected by a first screening and has an amino acid sequence having S at residue 91, W at residue 93, L at residue 94, S at residue 115, H at residue 117, W at residue 118, and one or more of the above-described residues at other residue positions of 67, 69, 72, 45, 47 and 49.

Likewise, in still another aspect, the present invention is directed to a polypeptide binding specifically to Taq DNA polymerase and having the following sequence, in which the polypeptide was selected by first screening and has an amino acid sequence having S at residue 91, W at residue 93, L at residue 94, S at residue 115, H at residue 117, and W at residue 118, and further containing R at residue 67, K at residue 69, and A at residue 72, which were selected by second screening, as well as one or more of the above-described residues at other residue positions 45, 47 and 49.

In one embodiment, the polypeptides having binding affinity for Taq polymerase according to the present invention are represented by any one of SEQ ID NO: 3 to 13.

However, the polypeptides according to the present invention are not limited to the above-described sequences, but include biological equivalents thereof. As used herein, the term "biological equivalents" refers to polypeptides which contain additional modifications added to the amino acid sequence disclosed herein, but have substantially the same activity as the polypeptide disclosed herein. Such modifications include, for example, a deletion, insertion and/or substitution of one or more residues in the amino acid sequence.

In one embodiment, the polypeptides having binding affinity for Taq polymerase according to the present invention include ones having one or more conservative amino acid substitutions.

As used herein, the term "conservative amino acid substitutions" refer to substitutions that do not substantially affect or reduce the activity of a certain polypeptide. For example, the polypeptide according to the present invention may contain 1 to 15 conservative amino acid substitutions, particularly 1 to 12 conservative amino acid substitutions, for example, 1, 2, 5, 7, 9, 12, or 15 conservative amino acid substitutions.

In one embodiment, the polypeptides represented by SEQ ID NO: 3 to 13 according to the present invention contain a conservative substitution that occurred at one or more of residues 91, 93, 94, 115, 117, 118, 67, 69, 72, 45, 47 and 49.

In another embodiment, the polypeptides represented by SEQ ID NO: 3 to 13 according to the present invention contain a conservative substitution that occurred at one or more residues in addition to residues 91, 93, 94, 115, 117, 118, 67, 69, 72, 45, 47 and 49.

In still another embodiment, the polypeptides represented by SEQ ID NO: 3 to 13 according to the present invention contain a conservative substitution that occurred at one or more residues other than residues 91, 93, 94, 115, 117, 118, 67, 69, 72, 45, 47 and 49 therein.

Conservative amino acid substitutions are known in the art, and are as shown in Table 1 below based on Blosum (BLOcks SUbstitution Matrix). These conservative amino acid substitutions are described in, for example, Creighton (1984) Proteins. W. H. Freeman and Company (Eds); and Henikoff, S.; Henikoff, J. G. (1992). "Amino Acid Substitution Matrices from Protein Blocks". PNAS 89 (22): 10915-10919. doi:10.1073/pnas.89.22.10915; WO2009012175 A1, etc.

TABLE 1

| Original Residue | Very Highly Conserved Substitutions | Highly Conserved Substitutions (from the Blosum90 Matrix) | Conserved Substitutions (from the Blosum65 Matrix) |
| --- | --- | --- | --- |
| Ala | Ser | Gly, Ser, Thr | Cys, Gly, Ser, Thr, Val |
| Arg | Lys | Gln, His, Lys | Asn, Gln, Glu, His, Lys |

TABLE 1-continued

| Original Residue | Very Highly Conserved Substitutions | Highly Conserved Substitutions (from the Blosum90 Matrix) | Conserved Substitutions (from the Blosum65 Matrix) |
| --- | --- | --- | --- |
| Asn | Gln; His | Asp, Gln, His, Lys, Ser, Thr | Arg, Asp, Gln, Glu, His, Lys, Ser, Thr |
| Asp | Glu | Asn, Glu | Asn, Gln, Glu, Ser |
| Cys | Ser | None | Ala |
| Gln | Asn | Arg, Asn, Glu, His, Lys, Met | Arg, Asn, Asp, Glu, His, Lys, Met, Ser |
| Glu | Asp | Asp, Gln, Lys | Arg, Asn, Asp, Gln, His, Lys, Ser |
| Gly | Pro | Ala | Ala, Ser |
| His | Asn; Gln | Arg, Asn, Gln, Tyr | Arg, Asn, Gln, Glu Tyr |
| Ile | Leu; Val | Leu, Met, Val | Leu, Met, Phe, Val |
| Leu | Ile; Val | Ile, Met, Phe, Val | Ile, Met, Phe, Val |
| Lys | Arg; Gln; Glu | Arg, Asn, Gln, Glu | Arg, Asn, Gln, Glu, Ser, |
| Met | Leu; Ile | Gln, Ile, Leu, Val | Gln, Ile, Leu, Phe, Val |
| Phe | Met; Leu; Tyr | Leu, Trp, Tyr | Ile, Leu, Met, Trp, Tyr |
| Ser | Thr | Ala, Asn, Thr | Ala, Asn, Asp, Gln, Glu, Gly, Lys, Thr |
| Thr | Ser | Ala, Asn, Ser | Ala, Asn, Ser, Val |
| Trp | Tyr | Phe, Tyr, | Phe, Tyr |
| Tyr | Trp; Phe | His, Phe, Trp | His, Phe, Trp |
| Val | Ile; Leu | Ile, Leu, Met | Ala, Ile, Leu, Met, Thr |

One embodiment of the present invention encompasses the amino acid sequences represented by SEQ ID NO: 3 to 13 and sequences containing conservative substitutions therein.

Particularly, the present invention encompasses sequences containing conservative substitutions that occurred at one or more of residues 45, 47, 49, 67, 69, 72, 91, 93, 94, 115, 117 and 118 in the amino acid sequences represented by SEQ ID NO: 3 to 13. For example, considering conservative substitutions, the polypeptide represented by SEQ ID NO: 13 according to the present invention may have an amino acid sequence wherein residue 45 is S, T, A or N; residue 47 is K, R, Q, E or N; residue 48 is A, S, G or T; residue 49 is I, L, V, M or F; residue 67 is R, K, Q or H; residue 69 is K, R, Q, E or N; residue 72 is A, S, G or T; residue 91 is S, T, A or N; residue 93 is W, Y or F; residue 94 is L, I, V, M or F; residue 115 is S, T, A or N; residue 117 is H, N, Q, R or Y; and residue 118 is W, Y or F.

Furthermore, considering variants having biologically equivalent activities as described above, it is encompassed by the present invention not only the amino acid sequences disclosed herein or polynucleotides encoding the same as described below also the sequences substantially identical to the sequences disclosed herein. The term "sequences substantially identical" refers to those showing preferably at least 61%, more preferably at least 70%, still more preferably at least 80%, most preferably at least 90% similarity to the sequence disclosed herein, when aligning sequences with the sequence disclosed herein so as to correspond to each other to the highest possible extent and analyzing the aligned sequences using algorithms that are generally used in the art. Methods of alignment of sequences for comparison are well-known in the art. Various programs and alignment algorithms are described in, for example, Smith and Waterman, *Adv. Appl. Math.* (1981) 2:482; Needleman and Wunsch, *J. Mol. Bio.* (1970) 48:443; Pearson and Lipman, *Methods in Mol. Biol.* (1988) 24: 307-31; Higgins and Sharp, *Gene* (1988) 73:237-44; Higgins and Sharp, *CABIOS* (1989) 5:151-3; Corpet et al., *Nuc. Acids Res.* (1988) 16:10881-90; Huang et al., *Comp. Appl. BioSci.* (1992) 8:155-65 and Pearson et al., *Meth. Mol. Biol.* (1994) 24:307-31. The NCBI Basic Local Alignment Search Tool (BLAST) (Altschul et al., *J. Mol. Biol.* (1990) 215:403-10) is available from the NBCI or the like, for use in connection with the sequence analysis programs such as blast, blastp, blasm, blastx, tblastn and tblastx. The BLAST be accessed at http://www.ncbi.nlm.nih.gov/BLAST/. A description of how to determine sequence identity using this program is available at http://www.ncbi.nlm.nih.gov/BLAST/blast_help.html.

In another aspect, the present invention is also directed to a polynucleotide encoding the polypeptide according to the present invention, a recombinant vector comprising the polynucleotide, and a cell having the recombinant vector introduced therein.

In one embodiment, the polynucleotides according to the present invention may be represented by SEQ ID NO: 14 to 24, but are not limited thereto, and also include polynucleotides modified due to degeneracy of amino acid-encoding sequences, as well as polynucleotides having substantial identity as described above.

In addition, the polynucleotides according to the present invention include polynucleotide DNA or RNA.

The polynucleotide according to the present invention may be introduced into a suitable vector for various purposes, for example, expression. For example, the polynucleotide according to the present invention may be operably linked to suitable regulatory sequences so as to express a target protein in a suitable host. Examples of the regulatory sequences include a promoter capable of initiating transcription, any operator sequence for regulating such transcription, a sequence encoding an appropriate mRNA ribosome-binding site, and a sequence regulating the termination of transcription and translation. Vectors and plasmids, into which the polynucleotide according to the present invention may be introduced, are not specifically limited as long as they are replicable in hosts. Any known vectors which may be selected depending on the intended use can be used, including natural or recombinant plasmids, phagemids, cosmids, viruses and bacteriophages. Examples of a phage vector or cosmid vector that may be used in the present invention include pWE15, M13, λMBL3, λMBL4, λIXII, λASHII, λAPII, λt11, Charon4A, Charon21A and the like, and examples of a plasmid vector that may be used in the present invention include pBR-, pUC-, pBluescriptII-, pGEM-, pTZ-, pCL- and pET-based vectors, for example, pACYC177, pACYC184, pCL, pECCG117, pUC19, pBR322, pMW118, pCC1BAC, pET-21a, pET-32a vectors and the like.

A vector comprising the polynucleotide according to the present invention may be introduced into a suitable host. The vector may be replicated or perform its function irrespective of the host genome or may be integrated into the genome itself.

Cells comprising either the polynucleotide of the present invention or a vector comprising the polynucleotide include eukaryotic cells and prokaryotic cells. Examples of the cells include, but are not particularly limited to, bacterial cells such as *E. coli, Streptomyces, Salmonella typhimurium* and the like; yeast cells; fungal cells such as *Pichia pastoris;* insect cells such as *Drosophila, Spodoptera,* and Sf9 cells; animal cells such as CHO, COS, NSO, 293, and Bowes melanoma cells; or plant cells.

The polynucleotides according to the present invention include DNA and RNA, and may be introduced into host cells in various forms suitable for expression. For example, the polynucleotide may be introduced into host cells in the form of an expression cassette which is a gene construct comprising all elements required for self-expression. The expression cassette generally includes a promoter operably linked to the polynucleotide, a transcription termination signal, a ribosome-binding site and a translation termination signal. The expression cassette may be in the form of a self-replicable expression vector. In addition, the polynucleotide may also be introduced into a host cell by itself and may be operably linked to a sequence required for expression in the host cell.

In another aspect, the present invention is also directed to a homo- or hetero-dimer composed of two polypeptide monomers according to the present invention, or a homo- or hetero-trimer composed of three polypeptide monomers according to the present invention.

The dimer or trimer according to the present invention may be configured such that the N- or C-terminal ends of the monomers face each other in the N-to-C-terminal direction, but the direction is not limited to a particular direction, as long as it shows the effect of the present invention.

For dimer or trimers, the polypeptides according to the present invention may be linked by a linker. Various linkers known in the art that do not affect the activity of the polypeptides of the present invention may be used. For example, reference may be made to Chichili et al., PROTEIN SCIENCE 2013 VOL 22:153-167. In one embodiment, a poly-glycine linker or an amino acid linker rich in glycine may be used. For example, a linker such as GGG, GGGGG, GGSSG or GGSGG may be used, but is not limited thereto.

In another aspect, the present invention provides a method for producing a polypeptide binding specifically to Taq DNA polymerase, the method comprising the steps of: (a) culturing a recombinant cell to obtain a culture; and (b) recovering the polypeptide from the cultured cell or the culture.

In the present invention, the step of culturing the recombinant cell is preferably performed by a known batch culture method, continuous culture method or fed-batch culture method, etc., but is not particularly limited thereto. Regarding culture conditions, pH may be appropriately adjusted (pH 5 to 9, preferably pH 6 to 8, most preferably pH 6.8) by using a basic compound (for example, sodium hydroxide, potassium hydroxide or ammonia) or an acidic compound (for example, phosphoric acid or sulfuric acid), and an aerobic condition may be maintained by introducing oxygen or an oxygen-containing gas mixture into the culture, and the culture may be performed at 20 to 45° C., preferably 25 to 40° C. for about 10 to 160 hours. However, the culture conditions are not limited thereto. The polypeptide produced by the culture may be released into the medium or may remain in the cell.

The culture medium that is used in the present invention may contain: as carbon sources, sugars and carbohydrates (e.g., glucose, sucrose, lactose, fructose, maltose, molasse, starch and cellulose), oils and fats (e.g., soybean oil, sunflower seed oil, peanut oil and coconut oil), fatty acids (e.g., palmitic acid, stearic acid and linoleic acid), alcohols (e.g., glycerol and ethanol), organic acids (e.g., acetic acid), and the like, which may be used alone or in a mixture; as nitrogen sources, nitrogen-containing organic compounds (e.g., peptone, yeast extract, gravy, malt extract, corn steep liquor, soybean meal powder and urea), or inorganic compounds (e.g., ammonium sulfate, ammonium chloride, ammonium phosphate, ammonium carbonate and ammonium nitrate) and the like, which may be used alone or in a mixture; as phosphorus sources, potassium dihydrogen phosphate, dipotassium hydrogen phosphate, sodium-containing salts corresponding thereto, and the like, which may be used alone or in a mixture; or essential growth-promoting materials such as other metal salts (e.g., magnesium sulfate or iron sulfate), amino acids and vitamins.

In the step of recovering the polypeptide produced in the culturing step of the present invention, the desired polypeptide may be recovered from the culture by use of a suitable method known in the art, depending on the culture method, for example, a batch, continuous or fed-batch culture method.

In another aspect, the present invention is also directed to various use of the polypeptide of the present invention or the nucleic acid (polynucleotide) encoding the same.

The polypeptide according to the present invention can bind to Taq DNA polymerase at low temperature, for example, 4° C. to 50° C., to inhibit the activity of the polymerase before the start of synthesis, thereby increasing the specificity of the polymerization reaction.

Thus, the polypeptide of the present invention or the nucleic acid encoding the same may be used in various applications which require the inhibition of the polymerase activity at certain temperature and reactivation at denaturation step.

In one embodiment, the present invention is directed to a hot-start PCR composition containing the polypeptide of the present invention as an active ingredient. The composition according to the present invention may further contain, in addition to the polypeptide of the present invention, components required for PCR, such as Taq polymerase, dNTP, a divalent cation such as $Mg^{2+}$ or $Mn^{2+}$, a salt, buffer, a preservative and/or an additive. Among the above components, examples of the sale include KCl and NaCl; examples of the buffer include Tris-HCl, and sodium-/potassium phosphate; examples of the preservative include glycerol; and examples of the additive include DMSO, but the scope of the present invention is not limited thereto. The hot-start PCR composition may be mixed with an enzyme having another activity, depending on the intended purpose or use thereof. For example, the composition may be used together with reverse transcriptase, uracil DNA glycosylase, Pfu DNA polymerase, dUTPase, or pyrophosphatase, and in this case, a composition for exhibiting the activity of the enzyme may additionally be used, or the composition may be modified.

In another embodiment, the present invention is directed to a hot-start PCR method that uses the present polypeptide or a composition containing the same. The method according to the present invention comprises the steps of: mixing components required for PCR amplification, for example, forward and reverse primers and a template, with the polypeptide of the present invention as described above or a PCR composition containing the polypeptide; and allowing the mixture to react under conditions enabling PCR. The conditions enabling PCR may include, for example, reaction at 95° C. for about 1 min, followed by 45 cycles, each consisting of denaturation at 95° C. for 10 sec, annealing at 60° C. for 15 sec, and synthesis at 72° C. for 20 sec, but are not limited to such conditions. Any person skilled in the art may select suitable conditions in view of the nature of template to be amplified, the nature of primers, the composition of buffer, etc.

In another embodiment, the present invention is also directed to the use of the polypeptide or a composition containing the polypeptide for hot-start PCR. For this use, reference may be made to the foregoing description.

In still another embodiment, the present invention is also directed to the use of the polypeptide or a composition containing the polypeptide for preparation of a hot-start PCR composition. For this use, reference may be made to the foregoing description.

Hereinafter, the present invention will be described in further detail with reference to examples. It is to be understood, however, that these examples are for illustrative purposes only and are not intended to limit the scope of the present invention.

EXAMPLES

Example 1

Selection of Polypeptide Binding Specifically to Taq DNA Polymerase by use of Random Phage Library Example 1-1

Construction of Repebody Library Based on Protein Structure

Repebody is a protein in which LRR repeating units having conserved leucine residues are continuously linked to each other to maintain the overall protein structure (modularity), like naturally occurring LRR proteins. Repebody also has a curvature structure and is structurally divided into a concave region and a convex region. The concave region is important in the recognition of biomolecules, and the convex region is important in the maintenance of the overall structure. In the concave region, a hypervariable region is located, like the complementarity determining region (CDR) of antibody, to mediate protein-protein interactions. Furthermore, the convex region has a well conserved sequence and plays an important role in maintaining the overall structure of LRR. The protein structure of this repebody was analyzed, and a random library was designed as described in the following manner.

Specifically, to avoid steric hindrance resulting from a non-designed C-terminal loop, 6 amino acid residues (residues 91, 93, 94, 115, 117 and 118) in the concave region of two consecutive mutant modules (LRRV modules 2 and 3) located in the N-terminal direction were selected. Next, using as a template a polypeptide having a sequence of SEQ ID NO: 2 from which one module (LRRV4) had been removed, a codon encoding each of the selected amino acids substituted with an NNK (N=A+G+C±T, K=G+T) degenerate codon, and mutagenic primers for constructing a library were synthesized such that the nucleotide sequence of the remaining convex region contained silent mutations.

Thereafter, using the primers, overlap PCR for two modules was performed to obtain library DNA (SEQ ID NO: 25).

The obtained library was inserted into pBEL118M (Sang-Chul Lee et al., "Design of a binding scaffold based on variable lymphocyte receptors of jawless vertebrates by module engineering," PNAS, 2012, 109(9), 3299-3304) to obtain a first library phagemid. Next, the obtained library was introduced into $E.\ coli$ XL1-Blue by electroporation to obtain a recombinant microorganism, thereby constructing a library having a synthetic variety of about $1.0 \times 10^8$.

Example 1-2

Selection of Polypeptide that Binds to Taq DNA Polymerase by Panning of Repebody Library Using the library constructed in Example 1-1, polypeptides capable of binding to Taq DNA polymerase were selected and purified. Specifically, in order to select candidates capable of binding to Taq DNA polymerase, Taq DNA polymerase was added to an immuno-tube at a concentration of 100 μg/mL, and coated at 4° C. for 12 hours. The coated immune-tube was washed three times with PBS, and blocked with a PBS buffer (TPBSA) containing 1% BSA and 0.05% Tween 20 at 4° C. for 2 hours. Next the purified phage was added to the coated immune-tube at a concentration of $10^{12}$ cfu/ml and allowed to react at room temperature for 2 hours. After completion of the reaction, the immune-tube was washed five times with a PBS buffer (TPBS) containing 0.05% Tween 20 for 2 minutes each time and washed twice with PBS. Finally, 1 ml 0.2 M glycine-HCl (pH 2.2) was added to the immune-tube and allowed to react at room temperature for 13 minutes, thereby eluting phages having displayed on the surface thereof repebody candidates capable of binding to Taq DNA polymerase. The eluate was neutralized by addition of 60 μL of 1.0 M Tris-HCl (pH 9.0), and added to 10 mL of host cell $E.\ coli$ XL1-Blue solution ($OD_{600}$=0.5), followed by plating on a 2×YT plate (bio-panning process). The bio-panning process was repeated four times in the same manner as described above. As a result, it was shown that phages binding specifically to Taq DNA polymerase were enriched by each panning process. The above result suggests that library phases binding to Taq DNA polymerase specifically increased.

Example 1-3

Determination of the Binding Activity of the First Selected Repebody to Taq DNA Polymerase and Sequencing of the Repebody ELISA analysis of the phages selected in Example 1-2 were done in the following manner by use of a 96-well plate coated with Taq DNA polymerase and BSA. Specifically, the 96-well plate coated with Taq DNA polymerase and BSA was blocked using TPBSA at room temperature for 1 hour. The phages having the repebody displayed thereon were added to each well of the plate to infect and incubated for 1 hour, followed by washing three times with TPBS. Next, each well was treated with a 1:5,000 dilution of HRP-conjugated anti-M13 monoclonal antibody (GE Healthcare) at room temperature for 1 hour and washed four times with TPBS. For signal detection, each well was treated with TMB solution (Sigma Aldrich) and treated with the same amount of 1N $H_2SO_4$ as the TMB, and then the absorbance at 450 nm was measured. Repebody candidates for which the absorbance ($OD_{450}$) of Taq DNA polymerase was at least 20 times higher than that of BSA were selected and sequenced to determine the amino acid sequences, and clones having the same amino acid sequence were excluded. As a result, it was shown that only a clone r-G6 did bind specifically to Taq DNA polymerase.

It was shown that r-G6 had an amino acid sequence wherein the amino acid isoleucine at position 91 was substituted with serine, the amino acid threonine at position 93 was substituted with tryptophan, the amino acid glycine at position 94 was substituted with leucine, the amino acid valine at position 115 was substituted with serine, the amino acid valine at position 117 was substituted with histidine, and the amino acid glutamic acid at position 118 was substituted with tryptophan (SEQ ID NO: 3). The above result indicates that residues playing an important role in binding to Taq DNA polymerase exist.

Example 1-4

Determination of Epitope of Selected Repebody

The epitope of the repebody binding to Taq DNA polymerase, obtained in Example 1-3, was determined. This is because whether or not the repebody can inhibit the activity of Taq DNA polymerase can be determined depending on the epitope.

Under this background, the clone r-G6 obtained in Example 1-3 was analyzed by ELISA as described above. The results are shown in FIG. 2. As a result, it was shown that the clone r-G6 did not bind to BSA, but did bind specifically to Taq DNA polymerase. Furthermore, when soluble Taq DNA polymerase (soluble Taq; sTaq) was added to the plate coated with Taq DNA polymerase, the signal of ELISA was reduced, suggesting that the selected repebody effectively binds to Taq DNA polymerase even in an aqueous solution. Finally, the clone r-G6 was analyzed by competitive ELISA using an antibody (JumpStart Antibody, Sigma Aldrich) known to bind to Taq DNA polymerase to inhibit the activity of the polymerase. As a result, the binding signal of the clone r-G6 was reduced by the antibody, indicating that the epitope of the clone r-G6 is similar to that of the antibody and that the clone r-G6 can be effectively used to inhibit the activity of Taq polymerase.

Example 2

Selection of Repebody Having Higher Binding Affinity for Taq DNA Polymerase by Use of Module-Based Mutagenic Method In order to further increase the binding affinity, a polypeptide having a higher level of binding affinity was selected using a module-based affinity improvement method as described in Korean Patent No. 1,356,076.

Although the clone r-G6 confirmed to bind specifically to Taq DNA polymerase in Example 1-3 had a dissociation constant of 134.4 nM for Taq DNA polymerase, an additional library was constructed in order to select a polypeptide capable of more effectively inhibiting the activity of Taq DNA polymerase.

Specifically, using a first module-based library for increasing affinity, mutagenesis was performed at a total of four amino acids (residues 67, 69, 71 and 72) in the LRRV1 module (FIG. 3), and a total of five panning processes were performed, thereby selecting three clones having increased binding affinity (SEQ ID NO: 4 to 6). The dissociation constants of the selected clones were measured using an isothermal titration calorimeter, and as a result, it was shown that the three clones all had increased binding affinities for Taq DNA polymerase.

Meanwhile, in order to develop mutants having further increased binding affinity, the clone r-G6E1 showing the highest binding affinity among the clones was used as a template polypeptide, and mutagenesis was performed at four residues 45, 47, 48 and 49 in the LRR1 module (FIG. 3), after which the same panning processes were performed, thereby selecting seven clones (SEQ ID NOs: 7 to 13). The dissociation constants of the selected clones were measured using an isothermal titration calorimeter, and as a result, it was shown that six clones had increased binding affinities for Taq DNA polymerase (FIG. 3) and the clone r-G6E1H8 showed the highest binding affinity (10.3 nM) for Taq DNA polymerase.

Through such results, the present inventors successfully obtained repebodies having binding affinity for Taq DNA polymerase, and confirmed that these repebodies are polypeptides having the ability to bind specifically to Taq DNA polymerase.

Example 3

Analysis of the Binding Affinity of Selected Repebody for Taq DNA Polymerase

The repebody selected in the above-described Example bind specifically to Taq DNA polymerase was confirmed by a phage-ELISA technique. The experiment was performed in the same manner as described in Example 1-3. As control proteins to which the repebody does not bind, mOrange fluorescence protein (Clontech), Lysozyme (Sigma Aldrich), His-tag antibody (Santa Cruz) and BSA (GenDEPOT) were used. The results of the analysis are shown in FIG. 4. As can be seen therein, the repebody r-G6E1H8 did bind specifically to Taq DNA polymerase compared to the controls.

Example 4

Analysis of Melting Temperatures of Selected Repebodies

In order to confirm the thermal stabilities of the repebodies selected in the above-described Example, an experiment for measuring the melting temperatures of the repebodies was performed. Using a J-815 CD spectrometer (Jasco, Japan), the molar ellipticity at 222 nm was measured over a temperature range from 30° C. to 80° C. Based on the results of the measurement, the melting temperature was calculated using a thermal denaturation analysis program (Jasco, Japan). The results of the calculation are shown in FIG. 5. As can be seen therein, the r-G6 had a melting temperature of 59.9° C., r-G6E1 had a melting temperature of 65.4° C., and r-G6E1H8 had a melting temperature of 62° C. Such results indicate that as the temperature in PCR reaction increases, the repebody is separated from Taq DNA polymerase by protein denaturation thereof, and that Taq DNA polymerase can initiate synthesis at an accurate extension temperature.

Example 5

Analysis of The Present Repebody to Inhibit Taq DNA Polymerase Activity

The repebody selected in the Example as described above were tested to confirm the inhibitory action of the repebody on the activity of Taq DNA polymerase in the following manner. First, 200 ng of Taq DNA polymerase was mixed with varying amounts of (0.05, 0.2, and 1.5 µg) of each of the repebodies (r-G6, r-G6E1, and r-G6E1H8) and allowed to stand at 4° C. for 15 minutes, thereby forming Taq DNA polymerase-repebody complexes. Each of the Taq DNA polymerase-repebody complexes was added to 50 µL of a reaction solution containing 1 nmol of dNTP, 12.15 pmol of [$^3$H]dTTP (0.1 Ci/mmol) and 2 mg/mL of activated calf thymus DNA. Each of the mixtures was allowed to react at 37° C. for 30 minutes, and then 11× stop buffer (110 mM EDTA, 2.2% SDS) was added thereto at a concentration of 1× to stop the reaction. Finally, the amount of radioactive DNA produced by Taq DNA polymerase was measured using a liquid scintillation counter, and based on the measured value, the percent inhibition of Taq DNA polymerase by the repebody was calculated.

The results of the calculation are shown in FIG. 6. As can be seen therein, the repebody having higher binding_affinity for Taq DNA polymerase also had a higher binding ability to inhibit the activity of Taq DNA polymerase. This indicates that the polypeptide developed in the present invention can inhibit the activity of Taq DNA polymerase, and thus can be effectively used in hot-start PCR.

Example 6

Hot Start PCR Using Repebody of the Present Invention

Example 6-1

Block PCR Using Repebody Binding to Taq DNA Polymerase

In order to evaluate the activity of the present repebody selected in Examples 1-3 to 2-1 above in increasing specificity and sensitivity of PCR, a block PCR was performed. Specifically, Taq DNA polymerase and each of the selected repebody polypeptides were mixed at a ratio of 1:10, and then added to a reaction buffer (10 mM Tris-HCl (pH 8.3), 20 mM KCl, 1.5 mM MgCl$_2$, 0.2 mM dNTP), thereby obtaining 20 µL of a real-time quantitative PCR mixture solution. Using human cDNA as a template, the GAPDH region was amplified using a forward primer (5'-CAAC-GAATTTGGCTACAGCA-3') and a reverse primer (5'-AGGGGTCTACATGGCAACTG-3'). The PCR reaction was performed under the following conditions: denaturation reaction at 95° C. for 1 minute, followed by 45 cycles each consisting of denaturation at 95° C. for 10 sec, annealing at 60° C. for 15 sec, and synthesis at 72° C. for 20 sec. The amplification products were then electrophoresed on agarose gel and stained with EtBr for visualization.

The results are shown in FIG. 8. As can be seen therein, in the absence of repebody the amplification signal was very weak when the template was present in minute amount (1 pg. In contrast, in the presence of hot-start PCR using the present repebody r-G6E1H8, the same GAPDH target was effectively amplified in a manner comparable to when the antibody was used. Particularly, when no template was added in the presence of antibody, some nonspecific amplification bands appeared. In contrast, when the repebody according to the present invention was used, no non-specific amplification occurred at all. This indicates that the repebody according to the present invention exhibits an excellent effect in increasing sensitivity and specificity when used in hot-start PCR.

Such results suggest that the repebody according to the present invention can effectively inhibit the activity Taq DNA polymerase in hot-start PCR and also can be very effectively separated from Taq DNA polymerase at a temperature equal to or higher than the denaturation temperature, indicating that the present repebody can be advantageously used for a very sensitive and specific amplification reaction.

Example 6-2

Real-Time PCR Using The Present Repebody

The activity of the repebody polypeptides selected in Examples 1-3 to 2-1 above to increase specificity and sensitivity was tested in real-time PCR as described in Example 6-1. To analyze the amplification products in real time, SYBR green I dye (Invitrogen) was added to a final concentration of 0.5×. As a template DNA, human cDNA was used in amounts of 100 pg (FIG. 9(*a*)), 10 pg (FIGS. 9(*b*)) and 1 pg (FIG. 9(*c*)), and was not used (FIG. 9(*d*)). FIG. 9 shows the results of real-time PCR performed to evaluate the hot-start PCR effects of the clones selected in the present invention. As can be seen therein, where a sufficient of amount of template DNA was added, an amplification product showing a desired melting peak (85° C.) was detected regardless of the method of performing hot-start PCR, but where a small amount (1 pg or less) of template DNA was added, Taq DNA polymerase showed a nonspecific amplification product (melting peak: about 75° C.) in the presence of no repebody or the repebody having slightly lower binding affinity. Among these repebodies, the use of the repebody r-G6E1H8 showed the highest specificity.

Example 6-3

Determination of Reactivation Time of Repebody during Hot-Start PCR

Using the finally selected repebody r-G6E1H8, the length of the initial activation time required for the repebody to exhibit the hot-start effect in real-time PCR was measured. The fundamental experimental method was the same as described in Example 6-1, real-time PCR using a TaqMan probe was performed in order to analyze amplification products in real time. Using human cDNA as a template, the β-actin region was amplified by PCR using a forward primer (5'-CCTGGCACCCAGCACAAT-3'), a reverse primer (5'-GCTGATCCACATCTGCTGGAA-3') and a TaqMan probe (5'-FAM-ATCAAGATCATTGCTCCTCCTGAGCGC-TA-MARA-3'). In the PCR, the initial activation time was set at various times (0.5, 1, 2, 5, 10 and 15 min). As controls, chemically modified Taq DNA polymerase (Enzynomics, Korean) and an antibody (JumpStart Antibody, Sigma Aldrich) were used. The results of the experiment are shown in FIG. 7. As can be seen therein, when the repebody was used, reactivation effectively occurred within 0.5 minutes at 95° C., like when the antibody was used. This indicates that the present repebody can be effectively used in hot-start PCR.

Example 7

Analysis of Repebody Dimer to Inhibit Taq DNA Polymerase Activity

The activity of a dimer of the repebody of the present invention in inhibition of Taq DNA polymerase was tested in the the following manner. Specifically, the selected r-G6E1H8 protein monomers were linked to each other by a linker consisting of three glycine amino acids, thereby constructing an r-G6E1H8 homodimer. The constructed homodimer vector was introduced and expressed in *E. coli*, and then separated and purified by a column chromatography technique. Using the obtained repebody dimer and the selected r-G6E1H8, the abilities of the dimer and the monomer to inhibit the activity of Taq DNA polymerase were measured according to the method described in Example 5.

The results are shown in FIG. 10. As can be seen therein, when the repebody monomer and the repebody dimer were used in the same amount (1 μg), the monomer showed an inhibition efficiency of 90%, and the dimer showed an inhibition efficiency of 94%. This suggests that the dimer formed of the repebody monomers can inhibit the activity of Taq DNA polymerase with an efficiency similar to or higher than that of the repebody monomer.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A repebody polypeptide which binds specifically to Taq DNA polymerase, the polypeptide consisting of an amino acid sequence selected from the group consisting of SEQ ID NOS: 3 to 13.

2. The repebpdy polypeptide of claim 1, wherein the polypeptide is present as a homo- or hetero-dimer or a homo- or hetero-trimer.

3. A polynucleotide encoding the repebody polypeptide of claim 1.

4. The polynucleotide of claim 3, wherein the polynucleotide is represented by the nucleotide sequence selected from the group consisting of SEQ ID NO: 14 to 24.

5. A recombinant vector comprising the polynucleotide of claim 3.

6. A transformed cell having introduced therein the polynucleotide of claim 3.

7. A hot-start Polymerase Chain Reaction (PCR) composition comprising the polypeptide of claim 1.

8. A hot-start PCR method, comprising the steps of:
mixing the polypeptide of claim 1 with a template and components required for PCR to obtain a mixture; and
allowing the mixture to react under conditions enabling PCR.

9. A transformed cell having introduced therein the recombinant vector of claim 5.

10. A hot-start PCR method, comprising the steps of:
mixing the PCR composition of claim 7 with a template and components required for PCR to obtain a mixture; and
allowing the mixture to react under conditions enabling PCR.

* * * * *

UNITED STATES PATENT AND TRADEMARK OFFICE
CERTIFICATE OF CORRECTION

PATENT NO. : 10,793,900 B2  
APPLICATION NO. : 15/575886  
DATED : October 6, 2020  
INVENTOR(S) : Hwang et al.

Page 1 of 1

It is certified that error appears in the above-identified patent and that said Letters Patent is hereby corrected as shown below:

In the Claims

Claim 2, Column 49, Line 56:  
Please delete "repebpdy" and replace with -- repebody --

Signed and Sealed this  
Ninth Day of February, 2021

Drew Hirshfeld  
*Performing the Functions and Duties of the*  
*Under Secretary of Commerce for Intellectual Property and*  
*Director of the United States Patent and Trademark Office*